United States Patent
Manabe et al.

(10) Patent No.: US 7,717,150 B2
(45) Date of Patent: May 18, 2010

(54) MANUFACTURING FACILITY OF ABSORBENT BODY, ABSORBENT BODY AND ABSORBENT ARTICLE

(75) Inventors: Sadanao Manabe, Shikokuchuo (JP); Hiroyuki Hanao, Shikokuchuo (JP); Takeshi Furudoi, Shikokuchuo (JP); Akinori Fukae, Shikokuchuo (JP); Toshikazu Maeda, Shikokuchuo (JP); Hiroyuki Yano, Shikokuchuo (JP); Taira Kubo, Shikokuchuo (JP); Yoshiharu Miyashita, Shikokuchuo (JP); Tomotsugu Matsui, Shikokuchuo (JP)

(73) Assignee: Daio Paper Corporation, Ehime (JP)

( * ) Notice: Subject to any disclaimer, the term of this patent is extended or adjusted under 35 U.S.C. 154(b) by 584 days.

(21) Appl. No.: 11/630,915

(22) PCT Filed: Jun. 28, 2005

(86) PCT No.: PCT/JP2005/011861

§ 371 (c)(1),
(2), (4) Date: Jul. 12, 2007

(87) PCT Pub. No.: WO2006/001456

PCT Pub. Date: Jan. 5, 2006

(65) Prior Publication Data

US 2008/0038504 A1 Feb. 14, 2008

(30) Foreign Application Priority Data

| Jun. 28, 2004 | (JP) | 2004-190409 |
| Nov. 25, 2004 | (JP) | 2004-340950 |
| Nov. 29, 2004 | (JP) | 2004-344715 |
| Feb. 8, 2005 | (JP) | 2005-031662 |
| Mar. 31, 2005 | (JP) | 2005-103856 |

(51) Int. Cl.
*B32B 37/00* (2006.01)
(52) U.S. Cl. .......... 156/497; 156/522; 156/578
(58) Field of Classification Search .......... 156/497, 156/500, 502, 516, 522, 555, 578, 580, 582
See application file for complete search history.

(56) References Cited

U.S. PATENT DOCUMENTS

| 6,086,950 | A | * | 7/2000 | Masaki et al. | 427/180 |
| 6,540,853 | B1 | * | 4/2003 | Suzuki et al. | 156/62.2 |
| 6,646,180 | B1 | | 11/2003 | Chmielewski | |
| 6,660,902 | B2 | | 12/2003 | Widlund et al. | |

FOREIGN PATENT DOCUMENTS

| CN | 2258390 | 7/1997 |
| CN | 1342446 | 4/2002 |

(Continued)

*Primary Examiner*—James Sells
(74) *Attorney, Agent, or Firm*—William L. Androlia; H. Henry Koda

(57) ABSTRACT

A shuffling hand feeling and unwanted non-uniform absorption characteristics in the case of using a tow (fiber bundle) are prevented.

An absorbent body includes a fiber aggregate 21 formed by opening the tow, a super absorbent polymer 54, and a sheet covering these components; and includes
the super absorbent polymer 54 bonded to the sheet 58 with an adhesive that is applied in a continuous plane to the entire surface or the substantially entire surface of at least the portion to be provided with the super absorbent polymer 54 in this sheet 58.

10 Claims, 29 Drawing Sheets

FOREIGN PATENT DOCUMENTS

| | | |
|---|---|---|
| CN | 1372451 | 10/2002 |
| CN | 1507336 | 6/2004 |
| JP | 9-273037 | 10/1997 |
| JP | H11-81116 | 3/1999 |
| JP | 2000-15093 | 1/2000 |
| JP | 2000-333992 | 12/2000 |
| JP | 2001-096654 | 4/2001 |
| JP | 2001-214399 | 8/2001 |
| JP | 2001-524350 | 12/2001 |
| JP | 2001-524399 | 12/2001 |
| JP | 2002-509764 | 4/2002 |
| JP | 2002-282304 | 10/2002 |
| JP | 2003-33397 | 2/2003 |
| JP | 2003-33398 | 2/2003 |
| JP | 2003-70820 | 3/2003 |
| JP | 2003-88555 | 3/2003 |
| JP | 2003-190210 | 7/2003 |
| JP | 2003-192732 | 7/2003 |
| JP | 2004-41339 | 2/2004 |
| WO | WO 2004/017883 | 3/2004 |

* cited by examiner

MANUFACTURING FACILITY OF ABSORBENT BODY, ABSORBENT BODY AND ABSORBENT ARTICLE

FIELD OF THE INVENTION

The present invention relates to absorbent articles such as paper diapers or sanitary napkins, absorbent bodies for use in absorbent articles, and manufacturing facilities of absorbent bodies.

PRIOR ART

Conventionally, absorbent bodies for use in body fluid absorbent articles are formed by loading pulp short fibers and super absorbent polymer particles on a loading drum, and thereafter packaging these components with an absorbent sheet such as crepe papers. On the other hand, recently, instead of an airformed core of short fibers, the use of tows (fiber bundles) made of fibers has been proposed (for example, refer to the Japanese Patent Application Laid-Open (JP-A) No. 2001-524399).

FIG. 29 shows structure of an absorbent body 120 using a conventional tow. In this absorbent body 120, a super absorbent polymer 122 is dispersed onto a strip-like tow 125, and thereafter packaged with a sheet 123 bead-applied with an adhesive 124.

Furthermore, as methods of manufacturing an absorbent body using such tow in a manufacturing line, the present applicants have developed the method in which an fiber aggregate made of continuous tow fibers is located in sequence on a continuous strip-like sheet, thereafter super absorbent polymer particles are dispersed onto the fiber aggregate as needed, and subsequently the strip-like sheet is folded to wrap the fiber aggregate containing the super absorbent polymers and thereafter is cut at predetermined intervals in MD direction (line conveying direction), to manufacture individual absorbent bodies.

However, by this method, a problem exists in that super absorbent polymers cannot be applied as intended with respect to a fiber aggregate. Furthermore, a problem exists also in that the product life of a cutter blade for use in cutting comes to be shorter than conventional ones, and that the super absorbent polymers are spilled out from cut points.

Moreover, also a manufactured absorbent body, in which almost no super absorbent polymer is held at a tow or a sheet, and can move freely without restraint, includes a problem in shuffling hand feeling, and unwanted non-uniform absorption characteristics such as the amount of absorption.

[patent document 1] Japanese Patent Application Laid-Open (JP-A) No. 2001-524399

DISCLOSURE OF THE INVENTION

Problems to be Solved by the Invention

Then, a main object of the present invention is to solve the above-mentioned problems.

Means to Solve the Problems

The present inventions having solved the above-mentioned problems are as follows.

<First Invention>

The first invention is an absorbent body including a fiber aggregate formed by opening tow, a super absorbent polymer, and a sheet covering them;

wherein an adhesive is applied in a continuous plane to the entire surface or the substantially entire surface of at least a portion to be provided with the super absorbent polymer in the sheet; and there is included the super absorbent polymer bonded with respect to the sheet with this adhesive.

Owing to such construction, since most super absorbent polymers are bonded to a sheet, the super absorbent polymers are hard to move, thus enabling to effectively prevent shuffling hand feeling, and unwanted non-uniform absorption characteristics.

<Second Invention>

The second invention is an absorbent body including a fiber aggregate formed by opening tow, a super absorbent polymer, and a sheet covering them;

wherein there are provided on the entire surface or the substantially entire surface of at least a portion to be provided with the super absorbent polymer in the sheet, a portion where an adhesive is applied, and a plurality of portions with no adhesive surrounded by the portion where the adhesive is applied; and there are included the super absorbent polymer bonded with respect to the sheet at the portion where the adhesive is applied, and the super absorbent polymer resided at the portion with no adhesive.

Owing to such construction, since super absorbent polymers are bonded to a sheet or surrounded by the portion applied with an adhesive, the super absorbent polymers are hard to move, thus enabling to effectively prevent shuffling hand feeling, and unwanted non-uniform absorption characteristics.

<Third Invention>

In the third invention according to the first or the second invention, there is included a super absorbent polymer bonded with respect to the fiber aggregate.

According to the third invention, since super absorbent polymers are bonded with respect to the fiber aggregate, it is possible to further effectively prevent shuffling hand feeling and unwanted non-uniform absorption characteristics.

<Fourth Embodiment>

The fourth invention is an absorbent body including a fiber aggregate formed by opening tow, a super absorbent polymer, and a sheet covering them;

wherein the amount of the super absorbent polymer at a first portion of the fiber aggregate is larger than the amount of the super absorbent polymer at a second portion of the fiber aggregate.

Like this, due to that there are provided the portion of a relatively large amount of super absorbent polymers and the portion of a relatively small amount thereof, it is possible to provide intended non-uniform absorption characteristics of an absorbent body.

<Fifth Invention>

In the fifth invention according to the fourth invention, the first portion is a width directional intermediate portion of the fiber aggregate, and the second portion is both width directional side portions of the fiber aggregate.

Like this, due to that the amount of super absorbent polymers at the width directional intermediate portion of a fiber aggregate is larger than the amount of super absorbent polymers at both width directional side portions of the fiber aggregate, in the case of use in absorbent articles, it is possible to ensure a larger amount of absorption at the portion to be provided with more liquids.

<Sixth Invention>

In the sixth invention according to the fourth invention, the first portion is a part in a longitudinal direction of the fiber aggregate, and the second portion is the other portions in a longitudinal direction of the fiber aggregate.

In the present absorbent body, the amount of the super absorbent polymers at one portion in a longitudinal direction is larger than the amount of the super absorbent polymers at the other portions, thus enabling to make absorption characteristics of an absorbent body different in the longitudinal direction.

<Seventh Embodiment>

In the seventh invention according to the sixth invention, there is substantially no super absorbent polymer at both of the longitudinal end portions.

According to the seventh invention, in the case of cutting at both longitudinal ends of an absorbent body when manufacturing, it is possible to prevent the product life of a cutter blade from being shorter.

<Eighth Invention>

The eighth invention is an absorbent body including a fiber aggregate formed by opening tow, a super absorbent polymer, and a sheet covering them;

wherein the density of the super absorbent polymer at the first portion of the fiber aggregate is higher than the density of the super absorbent polymer at the second portion of the fiber aggregate.

Due to that there are provided in a fiber aggregate the portion of a relatively high density of the super absorbent polymers and the portion of a relatively low density thereof, it is possible to provide intended non-uniform absorption characteristics such as absorption rate of an absorbent body.

<Ninth Embodiment>

In the ninth invention according to the eighth invention, the first portion is a width directional intermediate portion of the fiber aggregate, and the second portion is both width directional side portions of the fiber aggregate.

In this case, the rate of absorption at the width directional intermediate portion becomes low, and the rate of absorption at both side portions becomes high. As a result, in the case of use in absorbent articles, since liquids are spread around well from the portion to be fed with more liquids, it comes to be possible that a larger area is used for absorption. In addition, since the rate of absorption at both side portions is high, the so-called side leakage is prevented.

<Tenth Invention>

In the tenth invention according to the eighth invention, the first portion is a longitudinal intermediate portion of the fiber aggregate, and the second portion is a front-side portion and a rear-side portion of the longitudinal intermediate portion of the fiber aggregate.

In this case, achieved are absorption characteristics that the absorption rate at the longitudinal intermediate portion is low, and the rate of absorption at the front-side portion and the rear-side portion of the longitudinal intermediate portion is high. As a result, in the case of use in absorbent articles, since liquids are spread around well from the portion to be fed with more liquids, it comes to be possible that a larger area is used for absorption.

<Eleventh Invention>

The eleventh invention is an absorbent body including a fiber aggregate formed by opening tow, a super absorbent polymer, and a sheet covering them;

wherein the fiber density at the first portion of the fiber aggregate is higher than the fiber density at the second portion of the fiber aggregate.

A fiber aggregate formed by opening tow has properties of liquids being spread along the continuous direction of fibers, and this tendency becomes more marked as the density is increased. As a result, also by providing the portion of a relatively high fiber density of a fiber aggregate and the portion of a relatively low fiber density thereof, it is possible to provide intended non-uniform absorption characteristics of an absorbent body.

<Twelfth Invention>

In the twelfth invention according to the eleventh invention, the first portion is a width directional intermediate portion of the fiber aggregate, and the second portion is both width directional side portions of the fiber aggregate.

In this case, since spreading properties of body fluids at the width directional intermediate portion of a fiber aggregate is higher than spreading properties of body fluids at both width directional side portions. Consequently, in the case of use in body fluid absorbent articles, body fluids are likely to spread at the width directional intermediate portion to be fed with more body fluids, thus making it possible that a larger area is utilized for absorption. In addition, since body fluids are hard to spread at both width directional side portions, the so-called side leakage is effectively prevented.

<Thirteenth Invention>

The thirteenth invention is an absorbent body including a fiber aggregate formed by opening tow and a super absorbent polymer;

wherein the super absorbent polymer is dispersed in an internal part of the fiber aggregate, as well as bonded to a fiber via an adhesive.

In an absorbent body according to the present thirteenth invention, since super absorbent polymers are dispersed in an internal part of a fiber aggregate, as well as bonded to the fibers via an adhesive, as compared with the conventional methods in which merely the super absorbent polymers are dispersed with respect to the fiber aggregate, more super absorbent polymers will be reliably fixed in the fiber aggregate. Consequently, shuffling hand feeling is reduced. Furthermore, unwanted non-uniform absorption characteristic such as the amount of absorption is less likely to occur. That is, absorption characteristics can be made to be in intended embodiments, for example, uniform or non-uniform.

<Fourteenth Invention>

In the fourteenth invention according to the thirteenth invention, the fiber aggregate is 30 to 90 $g/m^2$ in fiber basis weight, the super absorbent polymer is a particulate super absorbent polymer in which the number of particles of size of 20 to 850 µm is not less than 90% a total number of particles, a basis weight of the super absorbent polymer with respect to the fiber aggregate is not more than 400 $g/m^2$, as well as a basis weight of an adhesive with respect to the fiber aggregate is not less than 1 $g/m^2$.

In case of employing such specified fiber basis weight, particle size of super absorbent polymers, basis weight of the super absorbent polymers, and basis weight of an adhesive, it is advantageous for exhibiting actions and effects according to the above-mentioned present inventions.

<Fifteenth Embodiment>

The fifteenth invention is an absorbent article comprising an absorbent body according to the first to fourteenth inventions.

According to an absorbent article of the present fifteenth invention, advantages of an absorbent body of the first to fourteenth inventions are provided.

<Sixteenth Invention>

The sixteenth invention is an absorbent body manufacturing facility comprising:

polymer application means for applying a super absorbent polymer with respect to an outer surface of a fiber aggregate that is formed by opening a tow; and polymer moving means for passing gas through a fiber aggregate applied with the super absorbent polymer, and causing the super absorbent polymer to move into the fiber aggregate by a passing force of gas.

According to the present sixteenth invention, since super absorbent polymers can be moved into a fiber aggregate using a passing force of gas, as compared with conventional methods of simple dispersion, more super absorbent polymers will be held well in the fiber aggregate. Therefore, it is possible to reduce shuffling hand feeling. Moreover, unwanted non-uniform absorption characteristics such as the amount of absorption are less likely to occur. That is, it is possible to make absorption characteristics in intended embodiments, for example, uniform or non-uniform.

<Seventeenth Invention>

In the seventeenth invention according to the sixteenth invention, there is provided covering means for putting a sheet on a face applied with a super absorbent polymer in a fiber aggregate; and polymer moving means makes suction from the side opposite to a face covered with the sheet in the fiber aggregate.

Like this, in case where in the state in which a sheet is located on one side of a fiber aggregate, suction is made on the opposite side thereof, a suction exerted on super absorbent polymers is increased, and thus the super absorbent polymers can be made to move more efficiently, to be preferred.

<Eighteenth Embodiment>

In the eighteenth invention according to the sixteenth or seventeenth invention, there is provided means for applying an adhesive with respect to a fiber aggregate before the super absorbent polymer is applied, or with respect to a fiber aggregate after the super absorbent polymer has been applied and before the super absorbent polymer is made to move into the fiber aggregate.

According to the present eighteenth invention, super absorbent polymers can be bonded with respect to a fiber aggregate, thus enabling to more effectively prevent shuffling hand feeling and unwanted non-uniform absorption characteristics. In other words, it is possible to make absorption characteristics in intended embodiments, for example, uniform or non-uniform. On the other hand, when manufacturing, since the super absorbent polymers are conveyed in the state the super absorbent polymers are bonded to the tow, it is possible to prevent polymers from being dropped off or scattered, or to prevent facility defects resulted therefrom.

<Nineteenth Invention>

In the nineteenth invention according to the eighteenth invention, there are provided opening means for opening a tow with a compressed air, and forming a fiber aggregate, and shield means for shielding air flowing from the opening means to the adhesive application means.

In the case where opening means using a compressed air is provided in the previous process of adhesive application means, there is a risk that the leaked compressed air flows into the adhesive application means along a fiber aggregate, and disturbs the provision of adhesives or makes the adhesives dried. In the invention according to this claim, these problems are prevented to occur by providing shield means.

<Twentieth Invention>

In the twentieth invention according to the seventeenth invention, there is provided means for applying an adhesive to a face to be on the side of the fiber aggregate in the sheet before the sheet is put on.

According to the present twentieth invention, super absorbent polymers can be bonded with respect to the sheet, it is possible to more effectively prevent shuffling hand feeling and unwanted non-uniform absorption characteristics.

<Twenty-first Invention>

In the twenty-first invention according to the seventeenth invention, there is provided no means for applying an adhesive to the sheet.

In the case where an adhesive is applied to a sheet in order to fix super absorbent polymers, or for other purposes, there is a possibility of an adhesive being adhered to facilities due to meandering or narrowing of tow (phenomenon of the width of a longitudinal intermediate portion is relatively narrowed by a conveying tension). Therefore, to prevent facility adhesion of adhesives and various problems to occur resulted therefrom, no adhesives are preferred to apply to the sheet.

<Twenty-second Invention>

In the twenty-second invention according to any one of the sixteenth to twenty-first inventions, there is provided means for applying an adhesive to a fiber aggregate after the super absorbent polymer has been moved into the fiber aggregate.

According to the present twenty-second invention, super absorbent polymers can be bonded to a fiber aggregate in the state of being moved as desired by suction. Consequently, it is possible to more effectively prevent shuffling hand feeling and unwanted non-uniform absorption characteristics.

<Twenty-third Invention>

In the twenty-third invention according to any one of the sixteenth to twenty-second inventions, the polymer application means applies a super absorbent polymer so that the amount of the super absorbent polymer at the first portion of the fiber aggregate is larger than the amount of the super absorbent polymer at the second portion of the fiber aggregate.

Due to that there are provided the portion of a relatively small application amount of super absorbent polymers and the portion of a relatively large application amount thereof, it is possible to achieve intended non-uniform absorption characteristics of an absorbent body.

<Twenty-fourth Invention>

In the twenty-fourth invention according to the twenty-third invention, the first portion is a width directional intermediate portion of the fiber aggregate, and the second portion is both width directional side portions of the fiber aggregate.

Like this, due to that super absorbent polymers are applied so that the amount of the super absorbent polymers at the width directional intermediate portion of a fiber aggregate is larger than the amount of the super absorbent polymers at both width directional side portions of the fiber aggregate, in the case of use in absorbent articles, it is possible to ensure a larger amount of absorption at the portion to be provided with more liquids.

<Twenty-fifth Invention>

In the twenty-fifth invention according to the twenty-third invention, the first portion is a longitudinal intermediate portion of the fiber aggregate, and the second portion is a front side portion and a rear side portion of the longitudinal intermediate portion of the fiber aggregate.

Like this, due to that super absorbent polymers are applied so that the amount of the super absorbent polymers at the longitudinal intermediate portion of a fiber aggregate is larger than the amount of the super absorbent polymers at the front side portion and the rear side portion of the longitudinal intermediate portion of the fiber aggregate, in the case of use in absorbent articles, it is possible to ensure a larger amount of absorption at the portion to be provided with more liquids.

<Twenty-sixth Invention>

In the twenty-sixth invention according to any one of the sixteenth to twenty-fifth inventions, the polymer moving means exerts the passing force of gas more strongly or in a longer time period with respect to the first portion of the fiber aggregate than the second portion of the fiber aggregate.

Like this, in case where there are provided the portion of a relatively strong passing force of gas and the portion of a relatively weak passing force thereof, or there are provided the portion of a relatively long operating time and the portion of a relatively short operating time, there will be the portion of a relatively large amount of super absorbent polymers being moved and the portion of a relatively small amount thereof in a fiber aggregate. As a result, there will be the portion of a relatively high density of the super absorbent polymers and the portion of a relatively low density thereof in the fiber aggregate. Consequently, it is possible to achieve intended non-uniform absorption characteristics such as absorption rate of an absorbent body.

<Twenty-seventh Invention>

In the twenty-seventh invention according to the twenty-sixth invention, the first portion is a width directional intermediate portion of the fiber aggregate, and the second portion is both width directional side portions of the fiber aggregate.

Like this, in case where the passing force of gas is made to exert strongly or longer with respect to the width directional intermediate portion of a fiber aggregate than both width directional side portions of the fiber aggregate, the amount of the super absorbent polymers being moved at the width directional intermediate portion is larger than that at both width directional side portions. As a result, the density of the super absorbent polymers at the width directional intermediate portion of the fiber aggregate becomes higher than the density of the super absorbent polymers at both width directional side portions of the fiber aggregate. Furthermore, in this case, the rate of absorption at the width directional intermediate portion comes to be low, and the rate of absorption at both width directional side portions comes to be high. Consequently, in the case of use in body fluid absorbent articles, since body fluids spread around well from the portion to be provided with more body fluids, it is possible to use a wider area for absorption. In addition, due to a higher absorption rate at both side portions, the so-called side leakage is prevented.

<Twenty-eighth Invention>

In the twenty-eighth invention according to any one of the sixteenth to twenty-seventh inventions, there is provided means that causes a fiber density at the first portion of the fiber aggregate to be higher than a fiber density at the second portion of the fiber aggregate.

A fiber aggregate formed by opening tow has properties of spreading liquids along the continuous direction of fibers, and this tendency comes to be more marked as the density becomes higher. Consequently, by providing the portion of a high fiber density and the portion of a low fiber density in the fiber aggregate, it is possible to achieve intended non-uniform absorption characteristics of an absorbent body.

<Twenty-ninth Invention>

In the twenty-ninth invention according to the twenty-eighth invention, the first portion is a width directional intermediate portion of the fiber aggregate, and the second portion is both width directional side portions of the fiber aggregate.

Due to that the fiber density at the width directional intermediate portion of a fiber aggregate is made higher than the fiber density at both width directional side portions of the fiber aggregate, spreading properties of body fluids at the width directional intermediate portion becomes better than spreading properties of body fluids at both width directional side portions. Consequently, in the case of use in body fluid absorbent articles, since body fluids are likely to spread at the width directional intermediate portion to be provided with more body fluids, it is possible to use a wider area for absorption. In addition, due to that body fluids are less likely to spread at both width directional side portions, the so-called side leakage is prevented.

<Thirtieth Invention>

The thirtieth invention is an absorbent body manufacturing facility comprising:

a conveyor line that conveys a fiber aggregate formed by opening a tow; and polymer application means for applying a super absorbent polymer while periodically changing an application amount with respect to a fiber aggregate on this conveyor line.

Like this, by providing polymer application means for applying super absorbent polymers with respect to a fiber aggregate while the application amounts are being periodically changed, it is possible to change absorption characteristics in a conveying direction, or to provide the portion with the super absorbent polymers and the portion with no super absorbent polymers.

<Thirty-first Invention>

In the thirty-first invention according to the thirtieth invention, there is no movement of a super absorbent polymer by a passing force of gas with respect to a fiber aggregate applied with the super absorbent polymer by the polymer application means.

In this case, it is possible to manufacture an absorbent body in structure that most super absorbent polymers are positioned outside a fiber aggregate, that is in a laminated structure including a layer made of the super absorbent polymers and a layer made of the fiber aggregate. Such absorbent body has such advantage as the rate of absorption comes to be higher when absorption is done from the layer of the fiber aggregate.

<Thirty-second Invention>

In the thirty-second invention according to the thirtieth or thirty-first invention, the polymer application means intermittently applies the super absorbent polymer in a conveying direction, to provide alternately in a conveying direction a portion at which the super absorbent polymer is applied, and a portion at which no super absorbent polymer is applied; and there is provided a cutter apparatus for cutting into individual absorbent bodies at the portion where no super absorbent polymer is applied.

As the present inventors have made intense studies in respect of the above-described shorter product life of a cutter blade, the hardness of super absorbent polymers to be generally used are found to be higher unexpectedly. The invention according to this claim has been made based on this finding, in which cutting can be made at the portions where almost no super absorbent polymer is resided by the intermittent application of the super absorbent polymers and by cutting at the portions to which no super absorbent polymers are applied, thus to prevent the product life of a cutter blade from being shorter. In addition, according to the invention defined as this claim, since there is resided at cutting points almost no super absorbent polymer, the super absorbent polymers are less likely to slip out from the cutting points, thus to prevent scattering of polymers or facility defects accompanied thereby. Further, the portion where no super absorbent polymers are applied is referred to as the portion where the basis weight of the super absorbent polymers is less than 0.01 g/cm$^2$.

EFFECTS OF THE INVENTION

As described above, according to the present inventions, the above-mentioned each advantage is achieved.

BEST MODE FOR CARRYING OUT THE INVENTION

Hereinafter, one preferred embodiment according to the present invention is described in detail referring to paper diapers as well as manufacturing facilities thereof shown in attached drawings.

<Examples of Pant-type Disposable Diapers>

FIG. 1 shows an example of pant-type disposable diapers. This pant-type disposable diaper 10 is provided with an exterior sheet 12 on the outside (backside) and an absorbent body 20 on the inside (front side). The absorbent body 20 is fixed to the exterior sheet 12. The absorbent body 20 is a part of receiving body fluids such as urines or soft stools (menstrual blood in the case of sanitary napkins as described below). The exterior sheet 12 is a portion with which a user wears the pant-type disposable diaper.

The exterior sheet 12 is hourglass-shaped as shown, and is narrow at the intermediate portion, to be regions on both sides through which a user puts his legs. Although the absorbent body 20 may have any shape, it is rectangular in the illustrated embodiment.

In the exterior sheet 12, as shown in FIG. 2, the absorbent body 20 is mounted and fixed in a predetermined position and thereafter folded in front and back, and a front body 12F and a back body 12B of the exterior sheet 12 are joined by heat sealing at junction regions 12A on both sides. Whereby, a pant-type disposable diaper including a waist opening WO and a pair of leg openings LO in structure shown in FIG. 1 is obtained.

There is shown the embodiment in which the width at the intermediate portion in a longitudinal direction (that is, in a vertical direction of FIG. 2. It is a front-back direction of a product as well) of an absorbent body 20 is smaller than the width at the narrow portion of the exterior sheet 12. The relation between these widths is vice versa, or the widths may be the same.

An exterior sheet 12 is desirably an embodiment that is made of, for example, two water-repellent non-woven cloths sheets, and provided with elastic stretching members interposed between these sheets to be fit to a user by elastic constrictive forces thereof. As this elastic stretching member, although a rubber thread or a strip of elastic foam, multiple rubber threads are desired to use. In the illustrated embodiment, rubber threads 12C, 12C . . . are continuously provided in the width direction in the waist region W, and provided only at both side portions in the sub-lumber region U, and are not provided in the crotch region L. Due to that the rubber threads 12C, 12C . . . are provided at both the waist region W and the sub-lumber region U, even if elastic constrictive forces of rubber threads 12C themselves are small, a paper diaper is in contact with a user also in the sub-lumber region U in its entirety. Thus, a product will be preferably fit to a user.

(Absorbent Body)

An absorbent body 20 according to the embodiment, as shown in FIG. 3, is provided with a top sheet 30 made of, for example, non-woven cloths allowing body fluids to permeate, an intermediate sheet (second sheet) 40, and an absorbent body 50 containing an absorbent core 56. Further, there is provided on the backside of the absorbent body 50 a body-fluid impermeable sheet (it is referred to as back sheet) 70 made of e.g., a plastic sheet. There is an exterior sheet 12 on the backside of this body-fluid impermeable sheet 70. Furthermore, there are provided barrier cuffs 60, 60 on both sides.

(Top Sheet)

The top sheet 30 possesses properties of allowing body fluids to permeate. Thus, as materials of the top sheet 30, what exhibits this body-fluid permeability will suffice, and, for example, porous or non-porous non-woven cloths, or porous plastic sheets may be exemplified. Moreover, non-woven cloths out of these materials are not particularly limited in material fibers thereof. Examples of these non-woven cloths include olefin-based synthetic fibers such as polyethylene or polypropylene, polyester-based synthetic fibers, or polyamide-based synthetic fibers; regenerated fibers such as rayon or cupra; natural fibers such as cottons; or fiber blend using these fibers in combination. Further, non-woven cloths may be manufactured by any processing. Examples of processing methods include known methods of spun lace, spun bond, thermal bond and melt blown processes, and by needle punching. In case of requiring flexibility or drapability, span lace process is preferred. In case of requiring high bulking power or softness, thermal bond process is preferred.

Furthermore, a top sheet 30 may be formed of one sheet, or a laminated sheet obtained by not less than two sheets being bonded. Likewise, the top sheet 30 may be formed of one sheet or not less than two sheets in a planer direction.

(Intermediate Sheet)

To cause body fluids having been permeated to transmit to an absorbent body, it may be provided an intermediate sheet 40 normally referred to as "second sheet" having a higher transmission rate than that of the top sheet 30. This intermediate sheet not only allows body fluids to immediately transmit to the absorbent body to enhance an absorption performance, but also prevents "reversing" phenomenon of absorbed body fluids from the absorbent body, thus enabling to make the top sheet 30 in a dry state all the time.

An intermediate sheet (second sheet) 40 is interposed between a top sheet 30 and a covering sheet 58. As shown in FIG. 20, an embodiment with no intermediate sheet (second sheet) 40 can be employed.

An intermediate sheet 40 according to an illustrated embodiment is located centrally shorter than the width of an absorbent core 56, but it may be provided across its entire width. The longitudinal length of the intermediate sheet 40 may be the same as the length of the absorbent core 56, or may within in a shorter length range with the region for receiving body fluids centered. A typical material of the intermediate sheet 40 is non-woven cloth of a superior permeability of body fluids.

Examples of materials of an intermediate sheet 40 may include the same material as a top sheet 30, spun lace, pulp non-woven cloth, mixed sheets of pulp and rayon, point bond or crepe papers. In particular, air-through non-woven cloth and spun-bond non-woven cloth are preferred.

The elasticity in front-back direction of products of an intermediate sheet is preferably 0.05 to 0.75 g·cm²/cm in order to reduce or eliminate the occurrence of shuffling discomfort in the case of touched from the front side of a product. Herein, "elasticity in front-back direction of a product" means the one obtained as values in the case where a sample cut in length of 200 mm and width of 20 mm is folded in the range of DFE sensitivity 20, curvature 0.0 cm$^{-1}$ to 0.5 cm$^{-1}$ using a pure bending tester ("KES-FB2" manufactured by Kato Tech Co., Ltd.). A covering sheet is also likewise.

(Absorbent Body)

An absorbent body 50 includes an absorbent core 56 having a fiber aggregate opened tows and super absorbent polymer particles, and a covering sheet 58 covering at least the backside and sides of this absorbent core 56. Furthermore, there is provided a holding sheet 80 between the absorbent core 56 and the backside site (lower portion) of the covering sheet 58.

First Embodiment of an Absorbent Body

FIG. 4 shows a first preferred embodiment of an absorbent body. This absorbent body 50 includes an absorbent core 56 having a fiber aggregate 21 and super absorbent polymer particles 54, and a covering sheet 58 covering at least the backside and sides of this absorbent core 56. The covering sheet 58 is applied with an adhesive 24 in a continuous plane at least on the entire surface or the substantially entire surface where super absorbent polymer particles are provided. Incidentally, "substantially entire surface" is referred to as 80% of the portions where super absorbent polymers are provided.

In further detail, a layer formed of super absorbent polymers 22 is provided via the adhesive 24 on the inside of the covering sheet 58, a layer formed of the fiber aggregate 21 is provided on the top thereof via the adhesive 25, and further the covering sheet 58 is bonded via the adhesive on the top of the fiber aggregate 21. The covering sheet 58 of the illustrated example is constructed to cover the fiber aggregate 21 and the super absorbent polymers 54 by being folded at both sides, but may employ an embodiment in which they are sandwiched between two vertical sheets to be packaged. As this covering sheet 58, as described below, preferably absorbent sheets such as crepe papers or non-woven cloths are used.

In addition, although not shown, there are provided on the entire surface or the substantially entire surface of at least the portion where super absorbent polymers are provided at a covering sheet 58 the portion to which an adhesive is applied, and a plurality of portions at which there is no adhesive surrounded by the portion applied with the adhesive. Thus, it may be constructed to include super absorbent polymers bonded with respect to the covering sheet 58 at the portion applied with the adhesive and super absorbent polymers resided at the portion with no adhesive.

In the case of applying an adhesive 24 in a continuous plane, curtain coating or roll coating may be used. In the case where there are provided the portion applied with an adhesive and a plurality of portions with no adhesive surrounded by the portions applied with the adhesive, spiral coating may be employed. As an adhesive 24, thermoplastic resins capable of being used in binders of the below-described fiber aggregate are preferably used.

In the present first example of an absorbent body, most super absorbent polymer particles 54 are bonded with respect to a covering sheet 58 with an adhesive 24, or a part of super absorbent polymer particles 54 are bonded with respect to the covering sheet 58 with the adhesive 24, as well as most super absorbent polymer particles 54 are contained in a closed space with no adhesive surrounded by the portions applied with the adhesive. Furthermore, a part or the whole of super absorbent polymer particles 54 are bonded with an adhesive 25 to the fiber aggregate 21. Thus, shuffling hand feeling and unwanted non-uniform absorbent characteristics can be effectively prevented. Moreover, a reference numeral 26 designates an adhesive for bonding the face opposite to the polymer side of the fiber aggregate 21 and the covering sheet 58 together.

Second Embodiment of an Absorbent Body

FIG. 5 shows a second embodiment of an absorbent body, and differs at a point of allowing super absorbent polymers 54 to be held also in a fiber aggregate 21 to the first embodiment.

Third Embodiment of an Absorbent Body

FIG. 6 shows a third embodiment of an absorbent body, and differs at a point that there are provided on both vertical sides of a fiber aggregate 21 respective super absorbent polymers 54 with respect to the first embodiment in which there is provided on one side (lower side) of the fiber aggregate 21 the super absorbent polymer 54. In this case, the super absorbent polymer 54 positioned on the upper side of the fiber aggregate 21 can be bonded using an adhesive 28 with respect to the fiber aggregate 21.

Fourth Embodiment of an Absorbent Body

FIG. 7 shows a fourth embodiment of an absorbent body, and is the one in which super absorbent polymers 54 are held also in a fiber aggregate 21 as is the second embodiment in the third embodiment.

Fifth Embodiment of an Absorbent Body

FIG. 8 shows a fifth embodiment of an absorbent body, and is an embodiment in which super absorbent polymers 54 bonded to a covering sheet 58 in the second embodiment, and an adhesive 25 for bonding thereof are omitted, and super absorbent polymers 54 are held only in a fiber aggregate 21.

Sixth Embodiment of an Absorbent Body

FIG. 9 shows a sixth embodiment of an absorbent body, in which there is additionally provided a layer 21B solely of a fiber aggregate (with no super absorbent polymer 54) on a fiber aggregate 21 holding super absorbent polymers 54, as well as in which the fiber aggregate 21 that holds the super absorbent polymer 54 and the layer 21B solely with a fiber aggregate are bonded together with an adhesive 26B.

Seventh Embodiment of an Absorbent Body

FIGS. 10 and 11 show a sixth embodiment of an absorbent body 50. This absorbent body 50 includes an absorbent core 56 having a fiber aggregate formed of tows made of fibers, and a super absorbent polymer, and a covering sheet 58 covering these components, and is characterized in that there are provided the portion of a relatively large amount of super absorbent polymer and the portion of small amount thereof. These more or less amounts are shown with shades of dots. Owing to such construction, it is possible to achieve intended non-uniform absorption characteristics, particularly the amounts of absorption.

Particularly as the illustrated example, it is a preferred embodiment that the amount of super absorbent polymers at a width directional intermediate part 50C of a fiber aggregate is larger than the amount of super absorbent polymers at both longitudinal side parts 50S of the fiber aggregate. In this case, when it is used in alignment with a width direction of an absorbent article (paper diaper DP in the illustrated example), a larger amount of absorption at the intermediate part 50C in a width direction to which more body fluids are fed can be assured.

Furthermore, as shown in FIG. 12, it is a preferred embodiment that the amount of super absorbent polymers at a longitudinal intermediate part 50M of a fiber aggregate is made larger than the amount of super absorbent polymers at a longitudinal front-back parts 50E of a fiber aggregate. In this case, when it is used in alignment with a longitudinal direction of an absorbent article (paper diaper DP in an illustrated example), a larger amount of absorption at the longitudinal intermediate part 50M to which more body fluids are fed can be assured.

In addition, it is a preferred embodiment that there is no super absorbent polymer at cut sites 50e at both longitudinal ends. When manufacturing, it is possible to prevent a shorter product life of cutter blades. An absorbent body according to such embodiment can be manufactured by setting application amounts of super absorbent polymer to be at three levels (much, less, and no), and repeating cycles consisting of much, less, and no.

On the other hand, in some cases, the amount of super absorbent polymers at both longitudinal end parts 50E, 50E may be made larger than the amount of super absorbent polymers at the longitudinal intermediate part 50M. Moreover, although in the illustrated example, an absorbent body 50 is longitudinally divided into three sections of an intermediate part and both end parts, it may be divided into two or not less than four sections to have different amounts of super absorbent polymers in respective sections, or the absorbent body 50 have amounts of super absorbent polymers continuously changed in a longitudinal direction.

In an absorbent body 50, super absorbent polymers may be held in a fiber aggregate or held on the fiber aggregate surface, or may be held in both. Furthermore, super absorbent polymers may be held partly on the fiber aggregate surface, and may be held in its entirety of the fiber aggregate.

However, at least in the region of receiving body fluids, preferably super absorbent polymer particles (SAP particles) are dispersed substantially across the thickness with respect to a fiber aggregate. This state in which the super absorbent polymer particles are dispersed substantially across the thickness is conceptually shown as an enlarged view of a principal part of FIG. 13. Furthermore, reference numeral 52 in FIG. 13 designates a component fiber (filament) of a fiber aggregate.

In case where there are no SAP particles at the upper, lower and intermediate portions of an absorbent core 56, it cannot be said to be "dispersed across the thickness." Therefore, embodiments of "dispersed across the thickness" include an embodiment in which SAP particles are dispersed "uniformly" across the thickness with respect to the fiber aggregate, and additionally an embodiment in which although they are "localized" at the upper, lower and intermediate portions, they are still dispersed in respective upper, lower and intermediates portions. In addition, an embodiment in which a part of SAP particles are not entered in a fiber aggregate, but remained on the surface thereof, an embodiment in which a part of SAP particles are passed through the fiber aggregate to be resided on a covering sheet 58, or an embodiment in which they are resided on a holding sheet 80 as shown in FIG. 14 are not to be excluded. Further, in the case of not considering gel blocking, SAP particles may be localized only at the upper or intermediate portions. In the case of considering no reversing, they may be localized only at the intermediate and lower portions.

Although in the seventh embodiment, there are larger or smaller amounts of super absorbent polymer particles at each part (hereinafter, referred to as dispersion density) in respect of at least one direction of a width direction, a longitudinal direction and a thickness direction of products, alternatively an embodiment in which amounts of super absorbent polymer particles are uniform in respect of all directions of a width direction, a longitudinal direction and a thickness direction of products may be employed.

Embodiments "of super absorbent polymer particles of different magnitudes of dispersion densities" are shown as follows. Now, as shown in FIG. 15, in an absorbent core 56, when letting a width direction of a product X, a longitudinal direction Y, and a thickness direction Z, as shown in Table 1, the case of making a dispersion density of respective super absorbent polymer particles larger (higher) than that in the other regions is defined as "gathering", and the case of the dispersion density of super absorbent polymer particles is the same is defined as "uniform", specific advantages of each embodiment will be as shown in Tables 2 to 4. It is a matter of course that respective conditions can be used in combination.

TABLE 1

| | | | | |
|---|---|---|---|---|
| X (width direction) | Near to center | Uniform | Near to edge | |
| Y (longitudinal direction) | Near to stomach | Near to center | Uniform | Near to back |
| Z (thickness direction) | Near to center | Uniform | Skin side | Underwear side |

TABLE 2

In respect of X direction, when "near to center", SAP can be provided efficiently at necessary sites, thus enabling manufacturing at low costs, as well as SAP loss at the time of manufacturing is less.

| X | Y | Z | Characteristic advantages | |
|---|---|---|---|---|
| Near to center | Near to stomach | Near to center | Advantageous for boys, less SAP discomfort. | (1) |

TABLE 2-continued

In respect of X direction, when "near to center", SAP can be provided efficiently at necessary sites, thus enabling manufacturing at low costs, as well as SAP loss at the time of manufacturing is less.

| X | Y | Z | Characteristic advantages | |
|---|---|---|---|---|
| | | Uniform | Advantageous for boys, good balance of absorption performance. | (2) |
| | | Skin side | Advantageous for boys, almost no reversing. | (3) |
| | | Underwear side | Advantageous for boys, high absorption rate. | (4) |
| | Near to center | Near to center | Advantageous for girls, less SAP discomfort. | (5) |
| | | Uniform | Advantageous for girls, good balance of absorption performance. | (6) |
| | | Skin side | Advantageous for girls, almost no reversing. | (7) |
| | | Underwear side | Advantageous for girls, high absorption rate. | (8) |
| | Uniform | Near to center | Advantageous for both boys and girls, less SAP discomfort. | (9) |
| | | Uniform | Advantageous for both boys and girls, good balance of absorption performance. | (10) |
| | | Skin side | Advantageous for both boys and girls, almost no reversing. | (11) |
| | | Underwear side | Advantageous for both boys and girls, high absorption rate. | (12) |
| | Near to back | Near to center | Advantageous for few month-old-babies e.g., newborn babies, less SAP discomfort. | (13) |
| | | Uniform | Advantageous for few month-old-babies e.g., newborn babies, good balance of absorption performance. | (14) |
| | | Skin side | Advantageous for few month-old-babies e.g., newborn babies, almost no reversing. | (15) |
| | | Underwear side | Advantageous for few month-old-babies e.g., newborn babies, high absorption rate. | (16) |

TABLE 3

In respect of X direction, when "uniform", discomfort with SAP is reduced, and less SAP movement in use is achieved.

| X | Y | Z | Characteristic advantages | |
|---|---|---|---|---|
| Uniform | Near to stomach | Near to center | Advantageous for boys, less SAP discomfort. | (17) |
| | | Uniform | Advantageous for boys, good balance of absorption performance. | (18) |
| | | Skin side | Advantageous for boys, almost no reversing. | (19) |
| | | Underwear side | Advantageous for boys, high absorption rate. | (20) |
| | Near to center | Near to center | Advantageous for girls, less SAP discomfort. | (21) |
| | | Uniform | Advantageous for girls, good balance of absorption performance. | (22) |
| | | Skin side | Advantageous for girls, almost no reversing. | (23) |
| | | Underwear side | Advantageous for girls, high absorption rate. | (24) |
| | Uniform | Near to center | Advantageous for both boys and girls, less SAP discomfort. | (25) |
| | | Uniform | — | (26) |
| | | Skin side | Advantageous for both boys and girls, almost no reversing. | (27) |

TABLE 3-continued

In respect of X direction, when "uniform", discomfort with SAP is reduced, and less SAP movement in use is achieved.

| X | Y | Z | Characteristic advantages | |
|---|---|---|---|---|
| | | Underwear side | — | (28) |
| | Near to back | Near to center | Advantageous for few month-old-babies e.g., newborn babies, less SAP discomfort. | (29) |
| | | Uniform | Advantageous for few month-old-babies e.g., newborn babies, good balance of absorption performance. | (30) |
| | | Skin side | Advantageous for few month-old-babies e.g., newborn babies, almost no reversing. | (31) |
| | | Underwear side | Advantageous for few month-old-babies e.g., newborn babies, high absorption rate. | (32) |

TABLE 4

In respect of X direction, when "near to edge", it is advantageous for the reduction in leakage around legs or from sides. In particular, it is superior for use with an inner pad.

| X | Y | Z | Characteristic advantages | |
|---|---|---|---|---|
| Near to edge | Near to stomach | Near to center | Advantageous for boys, less SAP discomfort. | (33) |
| | | Uniform | Advantageous for boys, good balance of absorption performance. | (34) |
| | | Skin side | Advantageous for boys, almost no reversing. | (35) |
| | | Underwear side | Advantageous for boys, high absorption rate. | (36) |
| | Near to center | Near to center | Advantageous for girls, less SAP discomfort. | (37) |
| | | Uniform | Advantageous for girls, good balance of absorption performance. | (38) |
| | | Skin side | Advantageous for girls, almost no reversing. | (39) |
| | | Underwear side | Advantageous for girls, high absorption rate. | (40) |
| | Uniform | Near to center | Advantageous for both boys and girls, less SAP discomfort. | (41) |
| | | Uniform | Advantageous for both boys and girls, good balance of absorption performance. | (42) |
| | | Skin side | Advantageous for both boys and girls, almost no reversing. | (43) |
| | | Underwear side | Advantageous for both boys and girls, high absorption rate. | (44) |
| | Near to back | Near to center | Advantageous for few month-old-babies e.g., newborn babies, less SAP discomfort. | (45) |
| | | Uniform | Advantageous for few month-old-babies e.g., newborn babies, good balance of absorption performance. | (46) |
| | | Skin side | Advantageous for few month-old-babies e.g., newborn babies, almost no reversing. | (47) |
| | | Underwear side | Advantageous for few month-old-babies e.g., newborn babies, high absorption rate. | (48) |

Eighth Embodiment of an Absorbent Body

Now, FIG. 16 shows an eighth embodiment of an absorbent body. This absorbent body 50 includes an absorbent core 56 containing a fiber aggregate and super absorbent polymers, and a covering sheet 58 covering these components, and is characterized in that there are provided the portion of a relatively high density of super absorbent polymers, and the portion of a relatively low density thereof. The higher or lower fiber densities are illustrated with gradation. In case where there are provided the portion of a relatively high density of super absorbent polymers and the portion of a relatively low density thereof in a fiber aggregate, it is possible to achieve intended non-uniform absorption characteristics, particularly the rates of absorption.

In particular, as in an illustrated example, it is a preferred embodiment that the density of super absorbent polymers at a width directional intermediate portion 50C is made higher than the density of super absorbent polymers at both width directional side portions 50S. In this case, achieved are such absorption characteristics as the absorption rate at the width directional intermediate portion 50C is low, and the absorption rate at both width directional side portions 50S is high. Thus, in the case of using this absorbent body in alignment with the width direction of an absorbent article, since much liquids are fed to the longitudinal intermediate portion at the width directional intermediated portion 50C, and spread around well therefrom, a wider area can be used for absorption. In addition, since the rate of absorption at both width directional side portions 50S is high, the so-called side leakage is prevented.

Ninth Embodiment of an Absorbent Body

Now, FIG. 17 shows a ninth embodiment of an absorbent body. This absorbent body 50 includes an absorbent core 56 containing a fiber aggregate and super absorbent polymers, and a covering sheet 58 covering these components, and is characterized in that there are provided the portion of a relatively high fiber density and the portion of a relatively low fiber density in the fiber aggregate. The magnitudes of these fiber densities are illustrated with the roughness and fineness of lines in the drawing. The fiber aggregate made of tows has characteristics of spreading liquids along a continuous direction of fibers, and this tendency comes to be marked as the density becomes higher. Thus, also by providing the portion of a relatively high fiber density and the portion of a relatively low fiber density in the fiber aggregate, it is possible to achieve intended non-uniform absorption characteristics of the absorbent body 50.

Such higher or lower fiber densities can be achieved by non-uniform opening such as partially strong opening at the time of manufacturing of a fiber aggregate, or by partially tying up a plurality of tows.

Particularly, as in the illustrated example, it is a preferred embodiment that the fiber density at a width directional intermediate parts 50C is made higher than the fiber density at both width directional side parts 50S. A fiber aggregate has such characteristics that the retention capacity of body fluids becomes higher in case of a lower fiber density, while spreading properties of body fluids becomes better in case of a higher fiber density. Therefore, when there are provided such different densities, body fluids are immediately spread at the width directional intermediate part 50C, and retention properties of body fluids are improved at both side parts 50S where no immediate spreading properties are required, thus to provide preferred characteristics to each site. More specifically, since spreading properties of body fluids at the width directional intermediate part 50C comes to be higher than spreading properties of body fluids at both width directional side parts 50S, in the case of using such absorbent body in alignment with the width direction of a body-fluid absorbent article, body fluids are likely to spread at the width directional intermediate part 50C where more liquids are fed, and thus a wider area can be used for absorption. In addition, since liquids are hard to spread at both width directional side portions 50S, the so-called side leakage is effectively prevented.

With no regard to how different fiber densities at both width directional side parts 50S and the width directional intermediate part 50C are, the fiber density at both side parts 50S is preferably 10 to 100 g/m$^3$, more preferably 20 to 70 g/m$^3$, most preferably 30 to 50 g/m$^3$. When the fiber density at both side parts 50S is too low, there is a risk of the occurrence of twisting in the width direction of a fiber aggregate. On the other hand, when the fiber density at both side parts is too high, there is a risk of providing discomfort to a user.

(Layout of an Absorbent Body)

In the case of using an absorbent body 50 in an absorbent article, any side may be used as the side of receiving body fluids. In particular, in the first embodiment, it is preferred to use so that the fiber aggregate 21 side (upper side in the drawing) is the side of receiving body fluids.

Furthermore, FIG. 18 shows layout examples of an absorbent body in paper diapers DP or sanitary napkins NP. A fiber aggregate formed of opened tows has such characteristics that body fluids are likely to spread in a continuous direction (flow direction) of fibers, while body fluids are hard to spread in a direction orthogonal to the continuous direction of fibers. Therefore, an absorbent body 60, as shown in FIGS. 18 (a) (b), is preferably provided so that the continuous direction of fibers (illustrated with multiple lines) is aligned with the longitudinal direction (front-back direction) of articles. As shown in FIGS. 18 (c) (d), however, the absorbent body 60 may be provided so that the fiber continuous direction thereof is along the width direction of articles. When letting the continuous direction of fibers the longitudinal direction of articles, liquids will be immediately spread also in the longitudinal direction, and thus the entire surface of the absorbent body 50 will be effectively utilized.

(Fiber Aggregate)

A fiber aggregate is formed by the method of opening a tow (fiber bundle), being a bundle of filaments regarded substantially continuous fibers that is an aggregate of filaments. Examples of tow component fibers may include polysaccharides or its derivatives (cellulose, cellulose ester, chitin, chitosan, and the like), synthetic high polymers (polyethylene, polypropylene, polyamide, polyester, polylactam amide, polyvinyl acetate, and the like). In particular, cellulose ester and cellulose are preferred.

Examples of celluloses include plant body-derived cellulose such as cotton, linter, or wood pulp, or bacteria cellulose, and may include regenerated cellulose such as rayon. The regenerated cellulose may be spun fibers.

Examples of cellulose esters capable of being preferably employed may include organic acid esters such as cellulose acetate, cellulose butyrate, and cellulose propionate; mixed acid esters such as cellulose acetate propionate, cellulose acetate butyrate, cellulose acetate phthalate, and cellulose nitrate acetate; and cellulose ester derivatives such as polycaprolactone-grafted cellulose ester. These cellulose esters may be used alone or in combination. The viscosity-average degree of polymerization of cellulose esters is, for example, 50 to 900, preferably about 200 to 800. The average degree of substitution of cellulose esters is, for example, about 1.5 to 3.0 (e.g., 2 to 3).

The average degree of polymerization of cellulose esters may be, for example, about 10 to 1000, preferably about 50 to 900, more preferably about 200 to 800. The average degree of substitution of cellulose esters may be, for example, about 1 to 3, preferably about 1 to 2.15, more preferably about 1.1 to 2.0. The average degree of substitution of cellulose esters may be selected in respect of e.g., improved biodegradability.

Cellulose esters may be preferably organic acid esters (for example, esters with organic acids having about 2 to 4 carbons), most preferably cellulose acetate. The acetylation degree of cellulose acetate may be about 43% to 62% in many cases, but may be preferably about 30% to 50% in respect of superior biodegradability. Cellulose ester is most preferably cellulose diacetate.

Tow component fibers may contain various additives, for example, a heat stabilizer, a colorant, a lubricant, a retention aid, and a whiteness improver.

The fineness of tow component fibers may be, for example, 1 to 16 deniers, preferably 1 to 10 deniers, more preferably about 2 to 8 deniers. Tow component fibers may be non-crimped fibers, but preferably crimped fibers. The degree of crimps of crimped fibers may be, for example, 5 to 75 numbers, preferably 10 to 50 numbers, more preferably 15 to 50 numbers per one inch. Furthermore, there are many cases of using crimped fibers evenly crimped. When using crimped fibers, bulky and light-weighted absorbent core can be manufactured, as well as highly integral tow can be easily manufactured due to entanglement between fibers. The cross sectional shape of tow component fibers is not particularly limited, but may be any one of circular, elliptical, heteromorphic (for example, Y-shaped, X-shaped, I-shaped, and R-shaped) or hollow shapes. Tow component fibers may be used in the form of tow (fiber bundle) made by tying up, for example, 3,000 to 1,000,000 numbers, preferably about 5,000 to 1,000,000 numbers of mono-filaments. A fiber bundle is preferably formed of about 3,000 to 1,000,000 numbers of bundled continuous fibers.

Since tow is poor in entanglement between fibers, mainly to keep configuration, binders acting to bond or fuse contact portions of fibers. Examples of binders include plasticizing esters such as triacetin, triethylene glycol diacetate, triethylene glycol dipropionate, dibutyl phthalate, dimethoxyethyl phthalate, and triethyl citrate ester, and additionally various resin adhesives, particularly thermoplastic resins.

Thermoplastic resins to be used as binders are resins that exhibit adhesion by fusion and solidification, and include water-insoluble or low water-soluble resins and water-soluble resins. Water-insoluble or low water-soluble resins and water-soluble resins may be used together as necessary.

Examples of water-insoluble or low water-soluble resins include, olefin-based mono or copolymers such as polyethylene, polypropylene, ethylene-propylene copolymer, and ethylene-vinyl acetate copolymer; acryl resins such as polyvinyl acetate, polymethyl methacrylate, methyl methacrylate-acrylic ester copolymer, and copolymer of (metha) acrylic monomer and styrenic monomer; stylene-based polymers such as polyvinyl chloride, vinyl acetate-vinyl chloride copolymer, polystylene, and copolymer of stylene-based monomer and (metha) acrylic monomer; polyesters that may be denatured; polyamides such as nylon 11, nylon 12, nylon 610, and nylon 612, rosin derivatives (for example, rosin esters), hydrocarbon resins (for example, terpene resins, dicyclopentadiene resins, and petroleum resins); and hydrogenerated hydrocarbon resins. These thermoplastic reins may be used alone or in combination.

Examples of water-soluble resins include various water-soluble high polymers, for example, vinyl water-soluble resins such as polyvinyl alcohol, polyvinyl pyrolidone, polyvinyl ether, and copolymer of vinyl monomer and copolymerizable monomer having carboxyl groups, sulfonic groups or salts thereof, polyalkylene oxides, water-soluble polyesters, and water-soluble polyamides. These water-soluble reins may be used alone or in combination.

Thermoplastic resins may be added with various additives such as antioxidant, stabilizer such as ultraviolet absorber, filler, plasticizer, preservative agent, and mildewproofing agent.

However, to the utmost extent, the use of binder components interrupting the entry of super absorbent polymer particles should be avoided. It is the best to use no binder components interrupting the entry of super absorbent polymer particles.

Tow can be manufactured by known methods, so that no detailed descriptions will be made. Bale of tow of cellulose diacetate capable of being preferably used in an absorbent body 50 is available from Celanese Corporation or Daicel Chemical Industries, Ltd. The bale of tow of cellulose diacetate is about 0.5 g/cm$^3$ in density and 400 to 600 kg in total weight.

Tow is peeled from this bale, and opened in a wide strip shape so as to have a desired size and bulk. The width of tow to be opened may be selected as needed, for example, 100 to 2000 mm in width, preferably about 100 to 300 mm of the width of an absorbent core of a product. Furthermore, by adjusting opening degrees of tow, the density of an absorbent core can be adjusted.

A fiber aggregate is preferably not more than 0.0075 g/cm$^3$, particularly preferably 0.0060 to 0.0070 g/cm$^3$ in fiber density when thickness is 10 mm. In case of excessively high fiber density, there will be less advantage in using a fiber aggregate formed by opening of tow, for example, light saving or thinning will be hard to achieve. Moreover, the basis weight of a fiber aggregate is preferably 30 to 300 g/m$^2$, particularly preferably 30 to 90 g/m$^2$. The basis weight of fibers can be adjusted by selection of tows to be a raw fabric, or manufacturing conditions thereof.

Examples of opening methods of tow include the method in which tow is entrained about a plurality of opening rolls, and tow is gradually enlarged in width as tow goes on to be opened, the method of repeating tension (elongation) and relaxation (contraction) to be opened, and the method of widening and opening with the use of a compressed air.

(Super Absorbent Polymer)

Super absorbent polymers include starched, cellulosic, or synthetic polymers, and may employ saponified substances of starch-acrylate (salt) graft copolymers or starch-acrylonitrile copolymers, crosslinking substances of sodium carboxymethylcellulose, or acrylate (salt) polymers.

Although the configuration of super absorbent polymers is preferably particulates that are normally used, other configurations may be used. Super absorbent polymer particles mean to include "powders" other than "particles". In terms of particle size, super absorbent polymer particles can employ those used in this type of absorbent articles as they are, for example, those of particle size of 20 to 850 μm. Specifically, super absorbent polymer particles of the following characteristics may be used.

mean particle size: about 350 μm
particle size distribution
850 μm on: 0%
500 μm on: 12.2%
250 μm on: 75.7%
180 μm on: 8.8%
106 μm on: 2.4%
106 μm pass: 0.9%
primary particle size: 110-120 μm Super absorbent polymers of any performance may be used without particular limitations, but those of the amount of water absorption of not less than 50 g/g are preferred. Further, super absorbent polymers of the speed of water absorption of not more than 45 seconds are preferably used. When the speed of water absorption exceeds 45 seconds, the so-called reversing in which body fluids having been fed into an absorbent body are reversed outside the absorbent body is likely to occur. In addition, super absorbent polymers of gel strength of not less than 900 Pa are preferably used. Whereby, by using tow, even in the case of a bulky absorbent core, sticky feeling after body fluids have been absorbed can be effectively suppressed.

The basis weight of super absorbent polymers may be suitably determined depending on the amount of absorption to be required for application of these absorbent bodies. Thus, this basis weight cannot be said with absolute certainty, but may be, for example, not more than 400 g/m². In case of excessively less basis weight of polymers, absorption performance cannot be kept. On the contrary, in case of excessively more basis weight, not only effects will be saturated, but also the above-described shuffling discomfort will be provided due to excess super absorbent polymer particles.

As described in the above-described seventh embodiment, super absorbent polymer particles can be adjusted in dispersion density or the amount of dispersion in a planer direction of an absorbent core 56. For example, there may be dispersed more super absorbent polymer particles at an excretion site of body fluids than other sites. In the case of considering a sex difference, a dispersion density (amount) on the front side is made higher for men, and a dispersion density (amount) at the central portion is made higher for women. Furthermore, there may be provided the portions with no presence of polymers locally (for example, in spotted pattern) in the planer direction of an absorbent core 56.

When necessary, a plurality of super absorbent polymer particles of different particle size distributions may be prepared, and dispersed and projected in sequence in a thickness direction. For example, there are located spaced apart in a line direction a plurality of the below-described super absorbent polymer particle dispersion means 90, previously super absorbent polymer particles of small particle size distribution are dispersed and projected, and thereafter super absorbent polymer particles of large particle size distribution are dispersed and projected, whereby those of small particle size distribution can be distributed on the lower side of an absorbent core 56, and those of large particle size distribution can be distributed on the upper side. This embodiment is advantageous for super absorbent polymer particles of small particle size distribution to enter the deep portion in a fiber aggregate.

The portion between super absorbent polymers and a fiber aggregate decides absorption characteristics. As the weight ratio in a planer area of 5 cm×5 cm in the region of directly receiving body fluids in an absorbent core 56, super absorbent polymers/fiber weight is preferably 1 to 14, particularly preferably 3 to 9.

(Size and Weight of an Absorbent Core)

On the other hand, as to the size of an absorbent core 56, a planer-projected area is preferably not less than 250 cm², as well as a thickness is preferably 0.5 to 10 mm, particularly preferably 1 to 5 mm. When the size of an absorbent core is within this range, it is extremely advantageous in order to improve a restoring force without the increase of weight, thickness, or costs. Further, an absorbent core is constructed to be preferably not more than 25 g, particularly preferably 10 to 20 g in weight. When the weight of an absorbent core is within this range, advantages provided by using no dedicated members come to be particularly marked.

(Compression Characteristics of an Absorbent Core)

The compression resilience RC of an absorbent core 56 is preferably 40 to 60%, particularly preferably 50 to 60%. Whereby, an absorbent core itself can come to exhibit a sufficient restoring force.

In addition, when the compression energy WC of an absorbent core 56 is 4.0 to 10.0 gf·cm/cm², since an article can be compressed to be compact at the same level or not less than the conventional level in packaging, it is preferred.

These compression characteristics may be adjusted by adjustment of the fiber density of a fiber aggregate by e.g., opening, selection of fiber materials, selection of types of binders such as plasticizers and adjustment of levels of processing, or combinations thereof.

Herein, compression energy (WC) is energy consumption in the case of pressing to 50 g (it is a thickness at this time in the embodiment) at the central portion of a test piece cut in length of 200 mm and width of 50 mm.

This compression energy can be measured using a handy compression tester (KES-G5, manufactured by Kato Tech Co., Ltd.). Measurement conditions in the case of using this tester, SENS: 2, the type of a force gauge: 1 kg, SPEED RANGE: STD, DEF sensitivity: 20, pressed area: 2 cm², taking in interval: 0.1 (standard), STROKE SET: 5. 0, and upper load: 50 gf/cm².

On the other hand, compression resilience (RC) is a parameter representing recoverability when fibers are compressed. Therefore, in case of high recoverability, compression resilience comes to be larger. This compression resilience can be measured using a handy compression tester (KES-G5, manufactured by Kato Tech Co., Ltd.). Measurement conditions in the case of using this tester are the same as in the case of the above-mentioned compression energy.

(Covering Sheet)

As a covering sheet 58, tissue papers, particularly crepe papers, non-woven cloths, polyethylene laminate non-woven cloths, sheets with micro-pores therethrough may be used. In this regard, sheets through which no super absorbent polymer particles are slipped out are desired. In the case of using non-woven cloths instead of crepe papers, hydrophilic SMMS (spun bond/melt-blown/melt-blown/spun bond) non-woven cloths are particularly preferred, and polypropylene, polyethylene/polypropylene and the like may be used as materials thereof. A basis weight thereof is preferably 8 to 20 g/m², particularly preferably 10 to 15 g/m².

This covering sheet 58, as shown in FIG. 3, may be in embodiment of enveloping the entire layer of a fiber aggregate and super absorbent polymer particles 54, and additionally, as shown in, for example, FIG. 19, may be in embodiment of covering only the backside and sides of this layer. Furthermore, not shown, the covering sheet 58 may be in embodiment that only the top and sides of an absorbent core 56 are covered with crepe papers or non-woven cloths, and the underside thereof is covered with a body fluid impermeable sheet such as polyethylene, or may be in embodiment that the top of an absorbent core 56 is covered with crepe papers or non-woven cloths, and the sides and underside thereof are covered with a body fluid impermeable sheet such as polyethylene (each material thereof will be the component of a covering sheet). As necessary, although the covering sheet 58 may be in embodiment that the layer of a fiber aggregate and super absorbent polymer particles 54 is sandwiched by vertical two-layer sheets, or in embodiment that the sheets are located only at the underside and top, movement of super absorbent polymer particles is hard to prevent, so that they are not desired embodiments.

(Holding Sheet)

There may be interposed between a holding sheet 80 and an absorbent core 56 super absorbent polymer particles 54 by e.g., dispersion thereof. There are some cases where super absorbent polymer particles 54 are slipped out of a fiber aggregate at the time of dispersion and projection to the fiber aggregate or at the process thereafter, or in the distribution process until consumers use. Concavo-convexes of super absorbent polymer particle groups having been slipped out of the fiber aggregate provide a shuffling discomfort when consumers touch them with hands when using. Then, there is interposed between an absorbent core 56 and a covering sheet 58 a holding sheet 80 having a holding function of absorbent polymers. This holding sheet 80 enforces the strength of papers insufficient solely with a covering sheet 58 such as tissue papers (crape papers), to reduce or prevent discomfort when consumers touch with hands at the time of using.

Furthermore, with reference to FIG. 14, conceptually is shown the case where there are provided super absorbent polymer particles under an absorbent core 56, or the case where super absorbent polymer particles having been contained in the absorbent core 56 are slipped out of a fiber aggregate, and gathered on a holding sheet 80 at stages from manufacturing until being used by consumers.

Materials of a holding sheet 80 are not particularly limited, but have only to function to hold absorbent polymers. Specifically, examples thereof include non-woven cloths, crimped pulps, low-absorbent cotton fibers (for example, non-degreased cotton fibers, degreased cotton fibers, rayon fibers processed with water-repellent agents or hydrophobic agents), polyethylene fibers, polyester fibers, acryl fibers, polypropylene fibers, silk, cotton, linen, nylon, polyurethane, and acetate fibers.

In the case of taking a non-woven cloth as a holding sheet 80, this holding sheet 80 may be non-woven cloth that is 0.01 to 10.00 gfcm/cm$^2$, preferably 0.01 to 1.00 gfcm/cm$^2$ in compression energy based on KES test, as well as 10 to 100%, preferably 70 to 100% in compression resilience. Further, the holding sheet 80 is preferably 0.05 to 0.75 g·cm$^2$/cm in elasticity in a front-back direction of a product in order to reduce or eliminate shuffling discomfort provided by super absorbent polymer particles. Herein, "elasticity in front-back direction of a product" means the one obtained as values in the case where a sample cut in length of 200 mm and width of 20 mm is folded in the range of DFE sensitivity 20, curvature 0.0 cm$^{-1}$ to 0.5 cm$^{-1}$ using a pure bending tester ("KES-FB2" manufactured by Kato Tech Co., Ltd.).

The reason why there is provided a holding sheet 80 is that absorbent polymers having been slipped off (slipped out) downward from the absorbent core 56 are held. Therefore, super absorbent polymer particles having been slipped out are brought in contact with users via a covering sheet 58 and a holding sheet 80, so that there is no risk of shuffling discomfort being transmitted to users. In particular, in case of non-woven cloths having the above-mentioned compression energy and compression resilience, functions as a holding sheet will be sufficiently exhibited.

Furthermore, since absorbent polymers having been slipped out are held by a holding sheet 80, and are not moved on a covering sheet 58, there is no fear of the occurrence of localization of absorption capacities. In particular, to prevent super absorbent polymer particles from moving on the holding sheet 80, there may be preliminarily applied on the holding sheet 80 e.g., hot melt adhesives having adhesion. Moreover, by making the top face of the holding sheet 80 (face opposite to the side to be used) a rough face, movement of super absorbent polymer particles on the holding sheet 80 may be prevented. Thus, examples of means of making rough or fuzzing include making a non-net face, not being a net face at the time of manufacturing non-woven cloths, marble machining, needle-punching, or brushing.

A holding sheet 80, as w shown in FIG. 3 and the like, may be located only below an absorbent core 56, or as shown in FIG. 14, may be go along the sides of the absorbent core 56 and turned up to the top thereof, to be extended. Furthermore, a plurality of holding sheets 80 may be used in a stack.

Although the above-mentioned example is the one in which there is provided a holding sheet 80 between an absorbent core 56 and a backside site of a covering sheet 58, the holding sheet 80 may be more backward than the covering sheet 58 (this embodiment is not shown), or a covering sheet 58 itself may be made to function as a holding sheet without an additional provision of a holding sheet 80. That is, if only there is provided a holding sheet on the backside with respect to an absorbent core 56, a shuffling discomfort in the case of being touched from the backside of a product will be reduced or will not occur.

(Body Fluid Impermeable Sheet)

A body fluid impermeable sheet 70 merely means a sheet located on the backside of an absorbent core 56, and in the present embodiment, is a sheet to interpose the absorbent core 56 between a top sheet 30 and this body fluid impermeable sheet 70. Thus, body fluid impermeable sheets are not particularly limited in materials thereof. Specifically, for example, olefin-based resins such as polyethylene or polypropylene, laminate non-woven cloths made by e.g., polyethylene sheet being laminated with a non-woven cloth, or non-woven cloths in which a water proof film is interposed to ensure a substantial liquid impervious properties (in this case, body fluid impermeable sheet is formed of a water-proof film and a non-woven cloth) are provided as an example. It may be a matter of course to be additionally provided as examples materials having liquid impervious properties as well as moisture permeability that are preferably used in recent years from the viewpoint of preventing sticky feeling. As sheets of these materials having liquid impervious properties as well as moisture permeability, may be provided as examples microporous sheets made by the process in which olefin-based resins such as polyethylene or polypropylene are admixed kneaded with an inorganic filler to mold sheets, and thereafter stretched in one or two axial directions.

A body fluid impermeable sheet 70 is extended on the face to be used in the form of the so-called wound around a forehead (not shown), thereby enabling to prevent side leakage of body fluids. In the present embodiment, this side leakage is prevented due to that there is interposed between double barrier sheets 64 forming barrier cuffs 60 a second body fluid impermeable sheet 72. According to this embodiment, the second body fluid impermeable sheet 72 is extended up to the rises of barrier cuffs 60, so that an advantage exits in that side leakage of body fluids rolling over a top sheet 30 and spread sideward or soft stools between the barrier cuffs 60, 60 can be prevented.

(Barrier Cuffs)

Barrier cuffs 60, 60 located at both sides of a product function to interrupt urines or soft stools rolling over a top sheet 30 and moved sideward, and to prevent side leakage, but are just additional elements.

The barrier cuffs 60 shown in the drawing are formed of double-layered barrier sheets, and configured to cover turned-in portions of a top sheet 30 from the backside of an absorbent core 56 to protrude on the front side. To interrupt urine rolling over the top sheet 30 and is moved sideward, particularly a body fluid impermeable sheet 70 are inserted at the sides between the double non-woven cloth sheets, and is extended on the way of the barrier cuffs 60 protruding to the front side.

In addition, although barrier cuffs 60 themselves can be designed in configuration as appropriate, in the illustrated example, elastic members, for example, rubber threads 62 are fixed under tension at tip portions and intermediate portions of protrusions of the barrier cuffs 60, and the barrier cuffs 60 are arranged to rise by an elastic constrictive force thereof in use states. Owing that the rubber threads 62 at the intermediate portion are positioned at the more central portion than the rubber threads 62, 62 at the tip portions, and fixed to the front and back end portions of a top sheet 30, as shown in FIG. 3, the barrier cuffs 60 are to be in embodiment to rise obliquely toward the central portion at the base portions, and to rise obliquely outward at the tip portions from the intermediate portions.

Materials of barriers sheets may be the ones having properties of permeating body fluids or the ones having properties of not permeating body fluids, and types thereof are not particularly limited. For example, the same materials as exemplified as a top sheet 30 and a body fluid impermeable sheet 70 may be used. In respect of e.g., preventing rash due to poor feel or friction, however, non-woven cloths are preferred, and bulky non-woven cloths such as air-through non-woven cloths are more preferred.

Furthermore, depending on functions to be considered important, respective water-repellent non-woven cloths or hydrophilic non-woven cloths may be used alone or in combination. For example, in case of considering important penetration prevention of body fluids or improvement in feel, preferred are water-repellent non-woven cloths, for example, water-repellent non-woven cloths coated with silicon-based, paraffin-based, alkyl chromic chloride-based water repellent agents. On the contrary, in case of considering important absorption of body fluids, hydrophilic non-woven cloths, non-woven cloths made of e.g., hydrophilic natural fibers, synthetic fibers, and regenerated fibers, as well as non-woven cloths made by hydrophilic-processing non-hydrophilic fibers with hydrophilizing agents.

(Elastic Member)

Elastic members have only to be elastic, and types thereof are not particularly limited.

For example, elastic hot melt, elastic films, rubber threads, and flat rubbers may be provided as an example. Examples of materials thereof may include styrene-based, olefin-based, urethane-based, ester-based rubbers, or foams of polyurethane, polyethylene, polystyrene, styrene butadiene, silicone, polyester or the like.

(Embossing)

There may be formed concaves E by embossing in a thickness direction from the front side of a top sheet 30. In this case, in addition to that embossed concaves E are formed only at the top sheet 30, as shown in FIG. 21 (*a*), embossed concaves E may be formed at both the top sheet 30 and an intermediate sheet 40; as shown in FIG. 21 (*b*), embossed concaves E may be formed so as to extend from the front side of the top sheet 30 to a part or substantially the whole in a thickness direction of an absorbent core 56; or as shown in FIG. 21 (*c*), embossed concaves E may be formed so as to extend from the front side of the top sheet 30 to a holding sheet 80. To allow embossed concaves E to form at both the top sheet 30 and the intermediate sheet 40, an intermediate sheet 40 is preferably within the range of 8 to 40 g/m$^2$ in basis weight, and preferably within the range of 0.2 to 1.5 mm in thickness, and a top sheet 30 is preferably within the range of 15 to 80 g/m$^2$ in basis weight, and preferably within the range of 0.2 to 3.5 mm in thickness in respect that sufficient embossing can be made on the conditions of not impairing liquid impervious properties.

In addition, embossed concaves may be formed only at the intermediate sheet 40 without formation of concaves at the top sheet 30, embossed concaves may be formed only at the absorbent core 56 without formation of concaves at the top sheet 30 and the intermediate sheet 40, or embossed concaves may be formed only at the absorbent core 56 without formation of concaves at the top sheet 30, the intermediate sheet 40 and the covering sheet 58.

Concaves E function to induce and spread body fluids in an extended direction thereof. Therefore, in case where the concaves E are made to be continuous substantially in grooves (including the case in which a plurality of concaves are aligned spaced apart to form one groove), body fluids will roll over the concaves E on the front side layer to be spread before reaching an absorbent core, and thus a wider portion of the absorbent core can be used for absorption. Accordingly, the absorption capacity of the entire product will be increased, to obtain an absorbent article in which leakage or reversing from sides due to an insufficient absorption capacity is hard to occur.

On the other hand, although an absorbent core 56 made of tow is likely to be lower in rigidity as compared with conventional pulp articles, rigidity is increased when embossed concaves are formed at the absorbent core 56, thus to be preferred. Although not shown, to increase rigidity of an absorbent body 50, it is also a preferred embodiment in which embossed concaves are formed in a thickness direction from the backside (the opposite side with respect to a top sheet 30) of the absorbent core 56. To form these concaves at the backside, embossing can be done integrally from the backside of a holding sheet 80, a covering sheet 58, a body fluid impermeable sheet 70 or an exterior sheet 12 up to the absorbent core 56. Furthermore, although these concaves on the backside are preferably formed along with the concaves E on the front side, only the concaves on the backside may be formed without formation of the concaves E on the front side. In the case of providing concaves on both the front side and the backside, the shapes of the concaves may be common on the front and back sides, or may be different on the front and back sides.

Embossed concaves function to induce and spread body fluids in an extended direction, and further to improve rigidity. Therefore, the embodiments of embossed concaves are desired to determine taking these effects into consideration. For example, concaves may be continuous substantially in grooves (including the case where a plurality of concaves are aligned spaced apart to form one groove), as well as a plurality of concaves may be formed spaced apart in a dotted manner. Furthermore, in terms of planar patterns, may be employed embodiments in which groove-like or dotted concaves are formed in a longitudinal direction, a width direction, in lattice of combination thereof, in a zigzag manner reciprocating in a width direction (staggered), or in irregular patterns of products. In addition, suitable embodiments such as pin-like, Mt. Fuji-like, and bellows-like patterns may be employed.

(Others)

Furthermore, respective components of an absorbent body 20 are fixed to each other with hot-melt adhesives and the like. In the case of application of adhesives, there may be intentionally provided applied portions and non-applied portions thereof at bonded surfaces. Moreover, adhesives can be applied by the methods of curtain coating, spiral coating, slot coating, control-seam coating (omega-shaped coating), or bead coating.

(Example of Tape-type Disposable Diapers)

On the contrary, FIGS. 22 and 23 show an example of tape-type disposable diapers. FIG. 23 is a view taken along the line 4-4 in FIG. 22, and illustrates an absorbent body 20 in rather exaggerated way.

A tape-type disposable diaper 10A is a diaper which includes fastening pieces attached to both side ends on the backside of the diaper, and includes hook elements at fastening faces of these fastening pieces, as well as in which a back sheet forming the backside of the diaper is to be a non-woven cloth laminate, and hook elements of fastening pieces can be engaged with any point on the surface of the back sheet when the diaper is worn.

An absorbent body 20 is the one in which an absorbent core 56 is interposed between a top sheet 30 and a body fluid impermeable sheet 70. This absorbent core 56 is enveloped at its entirety by a covering sheet 58 made of tissue paper, and is rectangular viewed in a plane. There is provided a holding sheet 80 between the absorbent core 56 and the covering sheet 58.

Furthermore, there is interposed an intermediate sheet 40 between the top sheet and the absorbent core 56. The body fluid impermeable sheet 70 is a rectangle wider than the absorbent core 56, and there is provided outward thereof a back sheet 12A made of non-woven cloth having an hourglass shape.

A top sheet 30 is a rectangle wider than an absorbent core 56, extended rather outward from the side edges of the absorbent core 56, and fixed to a body fluid impermeable sheet 70 with hot-melt adhesives.

There are formed at both side portions of a diaper barrier cuffs 60A protruding to the side to be used. These barrier cuffs 60A are formed of a barrier sheet 64 made of non-woven cloth continuous substantially in a width direction, and elastic members, for example, rubber threads 62 as one or plural numbers of elastic members around legs formed of rubber threads. Reference numeral 130 designates fastening pieces of hook and loop fasteners.

The interior of barrier sheets 64 has a leading end of fixing in a position spaced apart from the side edge of a top sheet 30, and fixed with e.g., hot-melt adhesives at the outward portions in a width direction from this fixing leading end to the extended edge of a body fluid impermeable sheet 70. The exterior of the barrier sheet 64 is fixed to a back sheet 12A at the underside thereof with e.g., hot-melt adhesives. Further, there are provided elastic members for gasket cuffs, for example, rubber threads 66.

The leading end fixed to a body fluid impermeable sheet 70 of the interior of the barrier sheets 64 forms an uprising end of the barrier cuffs 60A. Around the legs, the insides from these uprising ends are free portions not fixed to a product body, and these free portions are to rise up by an elastic constrictive force provided by rubber threads 62.

In the present example, by using hook and loop fasteners as fastening pieces 130, these fastening pieces 130 can be mechanically fastened with respect to a back sheet 12A. Thus, the so-called target tape can be omitted, as well as fastened positions with the fastening pieces 130 can be selected without restraint.

Fastening pieces 130 are bonded with, for example, adhesives at the bases of fastening backings made of plastics, poly laminate non-woven cloths, papers and the like, and include hook elements 130A on the tip sides. The hook elements 130A are bonded to the fastening backings with adhesives. The hook elements 130 include multiple engaging pieces on the outside thereof. There is included a temporary adhesive part 130B on the more distal side than the hook elements 130A. By the temporary adhesive parts 130B being bonded to the barrier sheets 64 at the final stage of product assembly, it is arranged to prevent the tip sides of the fastening pieces 130 from being peeled off. When using, the temporary adhesive parts 130B are peeled off against the adhesive force thereof, and the tip sides of the fastening pieces 130 are brought to the front body. The fastening backings are exposed on more distal sides than the temporary adhesive parts 130A to be tab parts to be grabbed.

There is provided on the inside of a back sheet 12A on the opening side of a front body a target printed sheet 74 as a design sheet. There is provided a target printing where designs to be targets of positions of fastening hook elements 130A of the fastening pieces 130 are made so as to be capable of being viewed through the back sheet 12A from the outside.

When a diaper is worn, the diaper is worn around a human body in a boat form, and then an elastic constrictive force from rubber threads 62 are exerted, so that the barrier cuffs 60A rise up by the elastic constrictive force provided by the rubber threads 62 around the legs.

The space surrounded by uprising portions forms the space in which urine or soft stools are confined. When urinated in this space, these urines are passed through a top sheet 30 to be absorbed in an absorbent core 56, as well as solid components of soft stools are prevented from being passed over with the uprising portions of the barrier cuffs 60A acting as barriers. If urines should pass over the distal uprising edges of the uprising portions to be leaked, side leakage is prevented owing to the stop function of planer bearing portions.

In the present embodiment, barrier sheets 64 forming respective uprising cuffs are desired not to have liquid permeability but to be substantially liquid impervious (may have liquid semi-permeability). Further, the barrier sheets 64 may be silicone-processed to have liquid repellent properties. In any event, the barrier sheets 64 and the back sheet 12A have air permeability respectively, as well as the barrier sheets 64 and the back sheet 12 are preferably sheets of anti-water pressure characteristics of not less than 100 mmH$^2$0 respectively. Whereby, air permeability is exhibited at the width directional sides of products, thus enabling to prevent sticky feeling of users.

Other points, for example, fabrics to use at each part are the same as the case of the above-described pant-type paper diaper, so that descriptions dare to be omitted.

Embodiments of Manufacturing Facilities

Now, manufacturing facility examples of an absorbent body will be described. FIG. 24 shows a manufacturing facility example of an absorbent body, in which a fiber aggregate 52Z of a continuous strip shape that is opened in a desired width and density. Upon opening, for example, as shown in FIG. 25, a tow 52Y is fed out in sequence from a tow bale 52X, in this conveying process, is sequentially passed through widening and opening means 120 using a compressed air and an opening section where there are a plurality of combined opening nip rolls 126A, 126B, 126C which circumferential speeds come to be higher as the rolls are positioned more downstream, to be widened and opened, thereafter passed through a binder adding box 140, and applied with a binder 140b (for example, and the box is filled with mist of triacetin), to obtain a fiber aggregate 52Z of a desire width and density. This opening line can be arranged to directly connect to the absorbent body manufacturing line of FIG. 24, and to feed the fiber aggregate 52Z having been manufactured directly to the absorbent body manufacturing line.

A fiber aggregate 52Z having been fed to the absorbent body manufacturing line may be applied with adhesives prior to application of super absorbent polymers. Thus, in an illustrated example, there is located an adhesive applicator 114 upstream of the position of dispersing polymers in a conveyor line. As adhesives, adhesives made of thermoplastic reins (specific examples are as described above) may be preferably used. The adhesives may be applied in a continuous plane by curtain coating or roll coating. There may be provided using spiral coating the portion applied with adhesives and a plurality of portions with no adhesives that are surrounded with the portions applied with adhesives. The amount of application of adhesives may be determined as appropriate, and is preferably not less than 1 $g/m^2$ in the normal case. However, in case of too much application, since the movement of super absorbent polymers is prevented, it is preferably determined to be in the range of 1 to 10 $g/m^2$.

Upon application of adhesives, in the case where opening means 110, 120 utilizing a compressed air are provided on the upstream side of the adhesive applicator, leaked compressed air AR flows into the adhesive applicator 114 along a fiber aggregate 52Z, and thus there is a risk of disturbing the feed of adhesives or making the adhesives dry. Therefore, preferably there is provided a shield 113 upstream of the adhesive applicator 114, and a compressed air AR is interrupted. This shield 113 is preferably disposed at least on the side of the adhesive applicator 114 of a fiber aggregate 52Z.

The fiber aggregate 52Z applied with an adhesive is subsequently dispersed with super absorbent polymer particles 54 on the top face by super absorbent polymer particle dispersing means. This dispersion may be achieved, for example, by merely causing super absorbent polymer particles to drop with one's own weight with respect to the fiber aggregate 52Z.

In this process, as needed, the dispersion amount of super absorbent polymer particles 54 may be periodically changed. Specifically, it is one preferred example in which the dispersing state and the non-dispersing state are repeated alternately, and then there are provided alternately in a conveyor direction the portion applied with super absorbent polymer particles 54 and the portion not applied therewith (super absorbent polymer particles are intermittently applied in a conveyor direction). In this case, as shown in FIG. 26, particularly preferably almost no super absorbent polymer particles 54 are dispersed at cut points C to be cut thereafter. In specific, particularly preferably, cut points C are determined spaced apart at intervals of a suitable length L1 that is rather shorter than the length of one absorbent body, for example, 10 to 30 cm in a conveyor direction, the portions of a length L2 inclusive of sufficient cut margins, for example, about 5 to 20 mm with these cut points C centered are brought in the state in which super absorbent polymer particles 54 are substantially absent across the width, and then cutting is done. Like this, the application process and the cutting process of super absorbent polymer particles 54 are harmonized, whereby as obvious from the below-described examples, much longer product life will be achieved as compared with the case of cutting at the portion provided with the super absorbent polymer particles 54.

There may be provided the portion of a large application amount and the portion of a small application amount by utilizing the periodical change of application amounts of super absorbent polymer particles 54. Further, application amounts may be continuously increased or decreased as well. In this case, may be employed an embodiment in which no super absorbent polymer particles are dispersed at cut points, as well as application amounts are increased as application points approach to the central portion in a conveyor direction between cut points.

In subsequent, although a fiber aggregate 52Z to which super absorbent polymer particles 54 have been dispersed is just rolled with a rolling roll, and fed to the subsequent process, it is a preferred example in which absorption is also made simultaneously with rolling with the use of a vacuum roll 106. This vacuum roll 106 have suction holes in the outer circumferential wall, and is arranged to suck with a suction pump, not shown, from the inside over a predetermined circumferential extent thereof (extent substantially on the left half in an illustrated example). The fiber aggregate dispersed with the super absorbent polymer particles 54 is guided while being guided on the outer circumferential surface by means of the vacuum roll 106. Furthermore, in this process, by making suction through suction holes of the vacuum roll 106, an atmosphere is passed from the application side of super absorbent polymer particles 54, through the fiber aggregate 52Z, to the opposite side (vacuum roll 106 side). By this passing force of gas, the super absorbent polymer particles 54 are made to move into the fiber aggregate 52Z.

In a particularly preferred embodiment, super absorbent polymer particles 54 are dispersed onto a fiber aggregate 52Z, and thereafter sheets such as a covering sheet 58 are further put thereon. In this case, in a vacuum roll 106, suction is made from the side opposite to the side of the fiber aggregate on which the sheet 58 is put on. Like this, when the sheet 58 is put on at the time of suction, as compared with the case with no sheet, a stronger suction force is exerted on the super absorbent polymer particles 54, thus enabling the super absorbent polymer particles 54 to efficiently move and disperse into an internal part of the fiber aggregate 52Z. Examples of these sheets include sheets having liquid permeability such as crepe papers, non-woven cloths, and perforated sheets, and liquid impervious sheets such as polyethylene films. Although, in the illustrated example, this sheet is only a covering sheet 58, in the case where there is provided the above-described holding sheet 80, a holding sheet, not shown, may be provided with the covering sheet 58, and suction may be done in the state in which these sheets are overlapped with the fiber aggregate 52Z.

To fix super absorbent polymer particles 54 to a fiber aggregate 52z, adhesives are applied to the fiber aggregate 52z before the super absorbent polymers are provided, as well as, not shown, adhesives may be applied to the fiber aggregate 52z after the super absorbent polymer particles 54 have been fed and before the super absorbent polymer particles 54 are allowed to move into the fiber aggregate 52z, that is, in the illustrated example, adhesives may be applied to the fiber aggregate 52z in the process from being fed with the super absorbent polymer particles 54 until entering the vacuum roll 106.

Furthermore, in the case where super absorbent polymer particles are dispersed on a fiber aggregate 52z, and thereafter sheets such as a holding sheet 80 and a covering sheet 58 are further put thereon, there may be provided in a sheet feed path with respect to a vacuum roll 106 an adhesive applicator 115, and adhesives may be preliminarily fed to a face to be the fiber aggregate 52z side of a sheet 58. In case of employing this embodiment, the super absorbent polymer particles 54 that are exposed on the surface of the fiber aggregate 52z are fixed to the sheet 58 via adhesives, and the super absorbent polymer particles 54 not having been bonded yet will be moved into an internal part of the fiber aggregate 52z by later suction. However, since there are a risk of the occurrence of such defects resulted from the adhesion of adhesives in the downstream facilities as adhesives are adhered to the vacuum roll 106 to lead to the occurrence of clogging, preferably adhesives dare not to be applied with respect to the sheet 58.

Furthermore, there may be provided an applicator 116 of adhesives on the side of a fiber aggregate 52z being exposed (the side opposite to the sheet 58, being the top in the drawing) downstream of a vacuum roll 106, and adhesives may be fed with respect to the fiber aggregate 52z after having been sucked, that is after the super absorbent polymer particles 54 have been moved. In case of employing this embodiment, the super absorbent polymer particles 54 having been moved to the side opposite to the side on which polymers have been applied in the fiber aggregate 52z out of applied super absorbent polymer particles 54 can be fixed. Moreover, in the case where an additional sheet is put on the exposed side of the fiber aggregate 52z, or both sides of a covering sheet 58 are folded around both ends of the fiber aggregate 52z to cover, the super absorbent polymer particles 54 having been moved to the exposed side of the fiber aggregate 52z can be fixed with respect to this sheet 58.

These adhesives may be applied alone or in combination. As adhesives, adhesives made of thermoplastic resins (as specifically described above) may be preferably used.

Further, a fiber aggregate 52z applied with super absorbent polymers 56 like this, for example, is covered with an additional sheet, or covered around both ends with both side portions of a sheet 58 to be folded with the use of a sailor, and thereafter cut in a predetermined length to be each absorbent body 50.

On the other hand, the amount distribution of super absorbent polymers, the density distribution of super absorbent polymers, and the fiber density distribution with respect to a fiber aggregate 52z are preferably uniform for general purposes. In the case of intending to exhibit special absorption characteristics, however, preferably there may be provided relatively more portions and relatively less portions, or relatively higher portions and relatively lower portions depending on the purpose thereof.

In specific, upon polymer dispersion, there may be provided the portions of relatively large dispersion amount and the portions of relatively small dispersion amount in a planar direction. In particular, in absorbent articles, there are many cases where the amount of absorption is required to increase at the width directional central portion of an absorbent body. In this case, when polymers are dispersed, the super absorbent polymers may be dispersed so that the amount of super absorbent polymers at the width directional intermediate portion of a fiber aggregate 52z is larger than the amount of super absorbent polymers at both width directional side portions of the fiber aggregate 52z.

Furthermore, upon polymer dispersion, the super absorbent polymers may be dispersed so that the amount of super absorbent polymers at the longitudinal central portion (at the longitudinal central portion of a part to be each absorbent body) of a fiber aggregate 52z is larger than the amount of super absorbent polymers at the front and rear portions in the longitudinal direction of the fiber aggregate 52z. Such dispersion can be achieved by periodically changing the amount of dispersion of the super absorbent polymer particles as described above.

In addition, by providing higher suction portions and lower suction portions at a vacuum roll 016, since the larger amount of super absorbent polymers are positioned on the vacuum roll 106 side as they are positioned in higher suction, there may be provided the portions of relatively high density of super absorbent polymers and the portions of relatively low density thereof in a fiber aggregate. For example, suction at the vacuum roll 106 is made to exert in more strength (or may be in a longer suction time period) with respect to the width directional intermediate portion of a fiber aggregate 52z than both width directional side portions of the fiber aggregate 52z, thereby, as in the above-described eighth embodiment, the density of super absorbent polymers at the width directional central portion of the fiber aggregate 52z can be made higher than the density at both width directional side portions of the fiber aggregate 52z. In such structure, since the absorption rate at the width directional central portion of the fiber aggregate 52z becomes lower, and the absorption rate at both width directional side portions becomes higher, in the case of use in absorbent articles, liquids are likely to spread all over the absorbent body, that is spreading properties are improved.

Furthermore, since in a fiber aggregate 52z made of tow, liquids are likely to flow along the continuous direction of fibers, by providing relatively high fiber density portions and relatively low fiber density portions, special absorption characteristics can be provided. Such arrangement may be achieved by e.g., partially strong opening at the time of manufacturing of the fiber aggregate 52z, or by partially using a bundle of a plurality of tows. As a specific example, as in the above-described ninth embodiment, it is a preferred embodiment in which the fiber density at the width directional intermediate portion of the fiber aggregate 52z, which is formed of tow, is made higher than the fiber density at both width directional side portions. Since in a fiber aggregate 52z made of tow, liquids are likely to flow along the continuous direction of fibers, more liquids will flow along the continuous direction of fibers at the width directional central portion of the fiber aggregate 52z.

In addition, no movement of super absorbent polymer particles 54 utilizing a passing force of gas may be done. Such embodiment, as shown in FIG. 24, may be achieved by applying the super absorbent polymer particles 54 to a fiber aggregate on the downstream side of a vacuum roll 106, or by omitting the suction by means of the vacuum roll 106.

Furthermore, super absorbent polymer particles 54 may be applied upstream of a vacuum roll 106, as well as the super absorbent polymer particles 54 may be applied to the fiber aggregate 52z also downstream of the vacuum roll 106. In this case, the super absorbent polymer particles 54 may be applied both on the upstream side ant the downstream side of the vacuum roll 106 all over the portion to be one absorbent body; or the super absorbent polymer particles 54 are applied upstream of the vacuum roll 106 with respect to a part of the portion to be one absorbent body, and the super absorbent polymer particles 54 are applied downstream of the vacuum roll 106 with respect to the other portions.

Moreover, as needed, in the case where super absorbent polymer particles 54 are applied downstream of a vacuum roll 106, particularly downstream of the vacuum roll 106 e.g., in the case where the super absorbent polymer particles 54 are applied to a fiber aggregate 52z downstream of the vacuum roll 106, at substantially the whole or a part of a conveyor line in an application position and after, suction is done from the underside via a sheet 58 and the fiber aggregate 52z, thus allowing the polymers to move further into the fiber aggregate 52z.

EXAMPLES

Experiment 1

Using a fiber aggregate including no super absorbent polymers (basis weight 0.000 g/cm$^2$) and a fiber aggregate of 0.020 g/cm$^2$ of super absorbent polymers, cutting was repeated until the blade of a cutter is nicked. As a result, by cutting at points of not including any super absorbent polymer or hardly including any super absorbent polymer, the product life of a cutter blade was found to lengthen by up to about 30%.

Experiment 2

With respect to a pant-type paper diaper provided with an absorbent body that is manufactured using a fiber aggregate made by opening tow of cellulose diacetate fibers (examples and comparative examples), and a general absorbent body and a product using pulp short fibers (conventional examples), the following measurement were made. Results are shown in Table 5 and Table 6.

As to the basis weight of super absorbent polymer particles (SAP), as shown in FIG. 27, the area in a plan view of an absorbent body, being a target is divided into a total of nine areas obtained by being equally divided into three in a width direction and being equally divided into three in a longitudinal direction, and the weights of super absorbent polymer particles with respect to each area are taken as dispersion densities.

Furthermore, test methods in the same Tables are as follows.

(Measurement of the Amount of Absorption of Super Absorbent Polymer Particles)

In 1 liter beaker provided with a rotor therein, 500.00±0.10 g of 0.9% hydrated chloride of sodium (guaranteed reagent of 9.00 g of sodium chloride was dissolved into 991.0 g of ion-exchange water to be prepared), 2.0000±0.0002 g of sample was added while the solution was being stirred with a magnetic stirrer, and the resultant solution therein was stirred for one hour with the beaker covered with Saran Wrap.

Contents in the beaker were filtered using a standard strainer (38 μm, 200 mm×45 mm), gel remained on the strainer was dewatered with Teflon plate and left for 15 minutes. The weight A of the gel remained on the strainer was measured, and the amount of absorption was calculated with the following expression.

$$C = A/S \quad (1)$$

Where: C: saline absorption amount (g/g), A: weight of gel remained on a strainer (g), S: sample weight (g)

(Measurement of the Amount of Absorption Under Pressure of Super Absorbent Polymer Particles)

As shown in FIG. 28, a cylinder 203 made of acryl resin (which is 2 cm in inside diameter, 5 cm in height, and in which a nylon net 201N of 75 μm is attached to the bottom) was installed in a standing position with the center thereof aligned with the vertical through hole at the central portion of a support platform 201, 0.100±0.0002 g of sample 200 was put in this cylinder 203, and a cylindrical weight 202 (1.9 cm in diameter, and 120 g in weight) was put on the sample 200.

The outlet of a burette 204 was connected to a lower opening of the through hole of the support platform 201 with a conduit tube 206, and scale values before valves V1 and V2 were opened and scale values after 30 minutes have passed were read.

The amount of absorption under pressure was calculated with the following expression.

$$C = (A-B)/S \quad (3)$$

Where: C: amount of absorption under pressure (ml/g), A: scale value when 30 minutes have passed after the start of water absorption (ml), B: scale value before water absorption (ml), S: sample weight (g)

(Measurement of Gel Strength of Super Absorbent Polymer Particles)

2.0 g of urea, 8.0 g of sodium chloride, 0.3 g of calcium chloride, 0.8 g of magnesium sulfate, 970.9 g of ion-exchange water, and 0.25 g of ferrous sulfate were mixed, to prepare 1 liter of artificial urine in total (50 ppm of iron ion).

49±0.1 g of artificial urine including 50 ppm of iron ion was put in a 100 ml beaker provided with a rotor therein and stirred using a magnetic stirrer. 1.0000±0.0002 g of sample was weighed and put in swirls in the beaker, and thereafter stirred until the swirls are disappeared and the liquid surface comes to be horizontal.

Gel having been produced was left for three hours in a machine at constant temperature and constant moisture of 40° C.×60% RH.

The gel was soaked in a constant-temperature water bath at 25° C. for five minutes, and thereafter gel strength was measured with neo-card meter. This measured values were unit-converted with the following expression, and thus gel strength (Pa) was calculated.

$$C = A \times 0.1 \quad (4)$$

Where: C: gel strength (Pa), A: gel strength obtained from neo-card meter (dyne/cm$^2$), 0.1: constant)

(Measurement of Reversing Amount in Diaper State)

A top sheet was put on an absorbent body cut in 100 mm×300 mm, and sealed on all sides to be a sample.

A cylindrical equipment of inside diameter of 27 mm (150 mm×150 mm in support part) was put at the center of a sample. The cylindrical equipment was made heavier as necessary.

The artificial urine of the amount of 50 cc was dripped three times at intervals of 10 minutes.

After 10 minutes after the third dripping, a filter paper (ADVANTEC No. 2, 10 cm×10 cm, thirty-ply) was put on, and applied with a load for 10 seconds with a weight of 5 kg. Thereafter, the weight of a kitchen paper was measured, the weight of the kitchen paper having been preliminarily measured into which the artificial urine has not been absorbed was subtracted, and the amount of artificial urine having been moved into the kitchen paper was calculated to be a reversing amount (g).

(Measurement of the Rate of Absorption in Diaper State)

An U-shaped equipment, which is made of an U-shaped plate formed supposing the portion from crotch to hip, and in which there is formed an inlet at the center in a width direction in the lowermost position, was used.

The center position in a longitudinal direction of an absorbent body in a diaper of sample was marked, this marked position was aligned with the inlet, and the sample was fixed to the outer surface of the U-shaped equipment.

The U-shaped equipment to which the sample was fixed was mounted on a hammock, and kept not to be inclined.

A weight (1 kg, 10 cm×10 cm) having a through hole in the center was mounted on the U-shaped equipment. At this time, the through hole of the weight was aligned with the inlet of the U-shaped equipment.

With respect to a sample, 100 cc of artificial urine (that is described above) was injected through the through hole of the weight and the inlet of the U-shaped equipment, and a time period taken to absorb the entire amount of artificial urine was measured to be the rate of absorption (seconds).

(Function Evaluation of Restoring Force)

Paper diaper samples were manufactured with using each absorbent body, and so as to be common except for the absorbent body. The ones that are not compressed after manufacturing, and the ones that are compressed in the common embodiment to be packaged, and thereafter the packages are opened were prepared. 20 test subjects made evaluations of restoring forces with visual observation and touch with hands. As a result, letting conventional examples a reference, as compared with this reference, the present absorbent bodies were evaluated to have high restoring force and sufficient softness (shown with evaluations of ◯ in Tables).

(Evaluation of Absorption Performance)

Dummies (for men and for women) of L size were prepared, in the case where 100 cc of artificial urine was injected at an injection rate of 12.5 cc/minute in each state of laid on its back, and face-down, evaluations were made with the number of times of rolling over until the occurrence of leakage.

TABLE 5

| | | Comparative Example 1 | Example 1 | Example 2 | Example 3 | Example 4 | Example 5 | Example 6 |
|---|---|---|---|---|---|---|---|---|
| Super absorbent polymer | SAP used amount [g] | 11 | 11 | 11 | 11 | 11 | 11 | 11 |
| | Absorption amount | 52 | 52 | 52 | 52 | 52 | 52 | 52 |
| | Absorption rate | 39 | 39 | 39 | 39 | 39 | 39 | 39 |
| | Absorption amount under pressure | 33 | 33 | 33 | 33 | 33 | 33 | 33 |
| | Gel strength | 1000 | 1000 | 1000 | 1000 | 1000 | 1000 | 1000 |
| Fiber aggregate | kinds | Acetate tow | Acetate tow | Acetate tow | Acetate tow | Acetate tow | Acetate tow | Acetate tow |
| | Fiber used amount [g] | 3.1 | 3.1 | 3.1 | 3.1 | 3.1 | 3.1 | 3.1 |
| Absorbent body | Area [m$^2$] | 0.0553 | 0.0553 | 0.0553 | 0.0553 | 0.0553 | 0.0553 | 0.0553 |
| | Thickness [mm] | 1.5 | 1.5 | 1.5 | 1.5 | 1.5 | 1.5 | 1.5 |
| | Fiber basis weight [g/m$^2$] | 56 | 56 | 56 | 56 | 56 | 56 | 56 |
| | SAP basis weight [g/m$^2$] | | | | | | | |
| | Area 1 | 199 | 278 | 159 | 159 | 199 | 199 | 199 |
| | Area 2 | 199 | 278 | 159 | 159 | 199 | 199 | 199 |
| | Area 3 | 199 | 278 | 159 | 159 | 199 | 199 | 199 |
| | Area 4 | 199 | 159 | 278 | 159 | 199 | 199 | 199 |
| | Area 5 | 199 | 159 | 278 | 159 | 199 | 199 | 199 |
| | Area 6 | 199 | 159 | 278 | 159 | 199 | 199 | 199 |
| | Area 7 | 199 | 159 | 159 | 278 | 199 | 199 | 199 |
| | Area 8 | 199 | 159 | 159 | 278 | 199 | 199 | 199 |
| | Area 9 | 199 | 159 | 159 | 278 | 199 | 199 | 199 |
| | average | 199 | 199 | 199 | 199 | 199 | 199 | 199 |
| | Z directional position of SAP | uniform | uniform | uniform | uniform | Near to skin side | Near to backside | intermediate |

| | | Example 7 | Example 8 | Example 9 | Example 10 | Conventional Example 1 | Conventional Example 2 |
|---|---|---|---|---|---|---|---|
| Super absorbent polymer | SAP used amount [g] | 11 | 11 | 11 | 21 | 11 | 11 |
| | Absorption amount | 52 | 52 | 52 | 52 | 53 | 53 |
| | Absorption rate | 39 | 39 | 39 | 39 | 45 | 45 |
| | Absorption amount under pressure | 33 | 33 | 33 | 33 | 33 | 33 |
| | Gel strength | 1000 | 1000 | 1000 | 1000 | 700 | 700 |
| Fiber aggregate | kinds | Acetate tow | Acetate tow | Acetate tow | Acetate tow | pulp | pulp |
| | Fiber used amount [g] | 3.1 | 3.1 | 3.1 | 3.1 | 9 | 3.9 |
| Absorbent body | Area [m$^2$] | 0.0553 | 0.0553 | 0.0553 | 0.0553 | 0.0553 | 0.0553 |
| | Thickness [mm] | 1.5 | 1.5 | 1.5 | 1.5 | 3.5 | 1.5 |
| | Fiber basis weight [g/m$^2$] | 56 | 56 | 56 | 56 | 163 | 70 |
| | SAP basis weight [g/m$^2$] | | | | | | |
| | Area 1 | 159 | 159 | 159 | 380 | 199 | 199 |
| | Area 2 | 159 | 159 | 159 | 380 | 199 | 199 |
| | Area 3 | 159 | 159 | 159 | 380 | 199 | 199 |
| | Area 4 | 278 | 278 | 278 | 380 | 199 | 199 |
| | Area 5 | 278 | 278 | 278 | 380 | 199 | 199 |
| | Area 6 | 278 | 278 | 278 | 380 | 199 | 199 |
| | Area 7 | 159 | 159 | 159 | 380 | 199 | 199 |
| | Area 8 | 159 | 159 | 159 | 380 | 199 | 199 |

TABLE 5-continued

| | | | | | | |
|---|---|---|---|---|---|---|
| Area 9 | 159 | 159 | 159 | 380 | 199 | 199 |
| average | 199 | 199 | 199 | 380 | 199 | 199 |
| Z directional position of SAP | uniform | uniform | uniform | uniform | uniform | uniform |

TABLE 6

| | | Comparative example 1 | Example 1 | Example 2 | Example 3 | Example 4 | Example 5 | Example 6 | Example 7 | Example 8 | Example 9 | Example 10 | Conventional example 1 | Conventional example 2 |
|---|---|---|---|---|---|---|---|---|---|---|---|---|---|---|
| Covering sheet | | present | present | present | present | present | present | present | present | present | present | present | present | present |
| Holding sheet | | present | present | present | present | present | present | absent | Present large elasticity | Present small elasticity | absent | present | absent | absent |
| Intermediate sheet | | present | present | present | present | present | present | present | present | present | absent | present | present | present |
| Absorption performance | Male dummy laid on its back [number] | 4 | 4 | 4 | 5 | 4 | 4 | 4 | 4 | 4 | 4 | 5 | 4 | 3 |
| | Male dummy face-down [number] | 2 | 3 | 2 | 1 | 2 | 2 | 2 | 2 | 2 | 2 | 3 | 2 | 1 |
| | Female dummy laid on its back [number] | 3 | 2 | 4 | 4 | 3 | 3 | 3 | 4 | 4 | 4 | 4 | 3 | 2 |
| | Female dummy face-down [number] | 3 | 4 | 4 | 2 | 3 | 3 | 3 | 4 | 4 | 4 | 4 | 3 | 2 |
| | Reverse amount [g] | 3.0 | 4.0 | 2.2 | 4.0 | 2.0 | 3.5 | 3.3 | 2.1 | 2.4 | 2.2 | 1.9 | 7.0 | 7.3 |
| | Absorption rate [sec] | 263 | 295 | 231 | 292 | 261 | 199 | 268 | 222 | 241 | 332 | 202 | 238 | 328 |
| Shuffling feel | Functions | ◎ | ◎ | ◎ | ◎ | ◎ | ◎ | ◎ | ◎ | ○ | Δ | Δ | ◎ | X |
| Restoring force (softness) | functions | ◎ | ◎ | ◎ | ◎ | ◎ | ◎ | ◎ | Δ | ○ | Δ | ○ | X | X | covering sheet: all are crepe papers 20 gsm holding sheet is present, and intermediate sheet is present: air-through non-woven cloth (30 gsm, PE/PET 2.2 dtex, fiber length 44 mm, eccentric 50%, durable and hydrophilic, PE/PET 2.8 dtex, fiber length 51 mm, eccentric and hollow 50%, durable and hydrophilic, manufactured by Fukuron Co., Ltd.) is used (elasticity B 0.300 gfc m$^2$/cm) holding sheet of example 7: air-through non-woven cloth (50 gsm, PE/PP 5.6 dtex,crimped fiber length 51 mm, water repellent, manufactured by Fukuron Co., Ltd.) is used (elasticity B 0.850 gfc m$^2$/cm) holding sheet of example 8: (SMMS, 13 gsm, PP 100%, manufactured by TSI Corporation) is used (elasticity B 0.03 gfc m$^2$/cm)
L size is used in dummy test
"large elasticity" means that elasticity is excessively large, and "small elasticity" means that elasticity is excessively small.

INDUSTRIAL APPLICABILITY

The present invention is preferred for manufacturing an absorbent body in absorbent articles such as paper diapers, sanitary napkins, incontinence pads, and absorbent pads used together with a diaper cover.

Description of Reference Numbers

Figure 1:
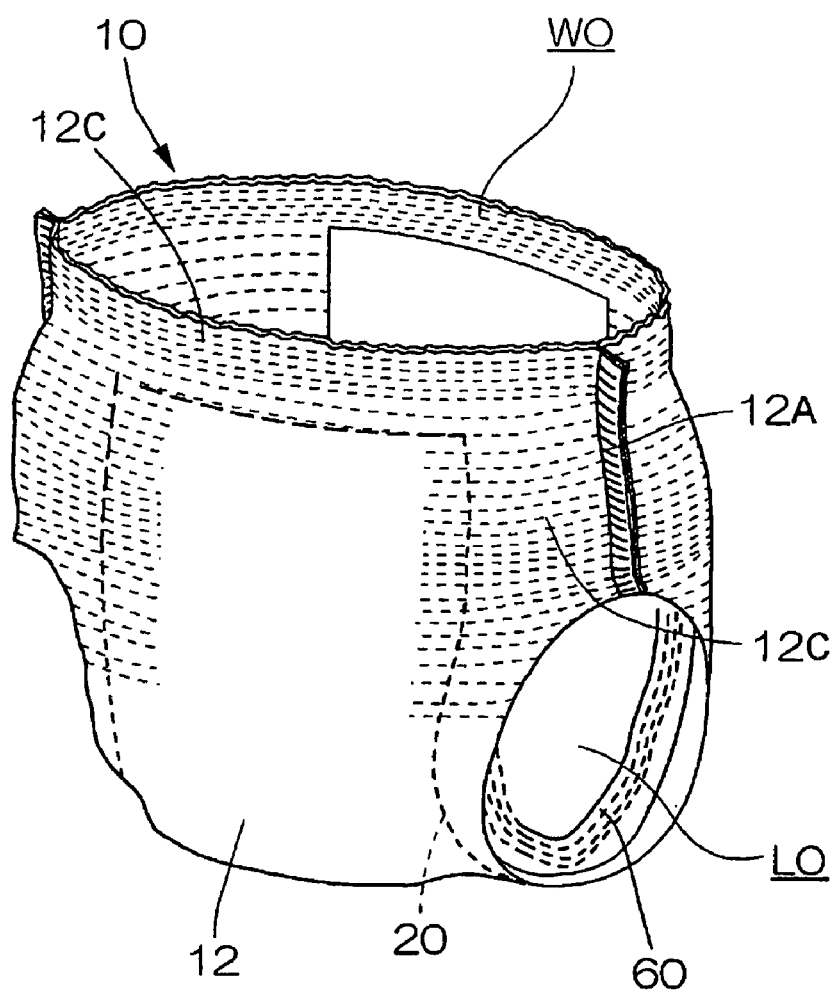
FIG. 1 is a perspective view showing a pant-type diaper.
Figure 2:
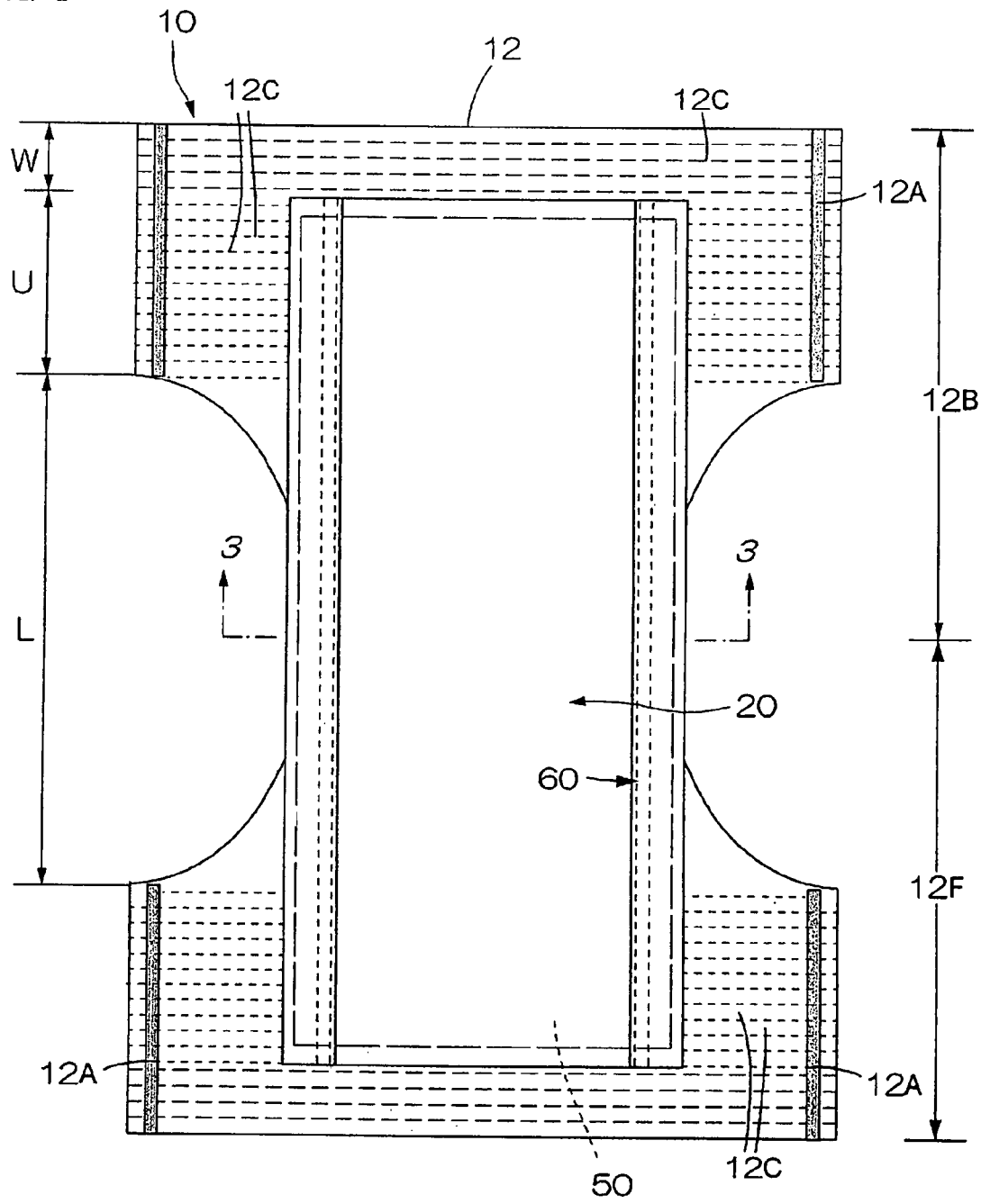
FIG. 2 is a plan view showing a pant-type diaper in a deployed state.
Figure 3:
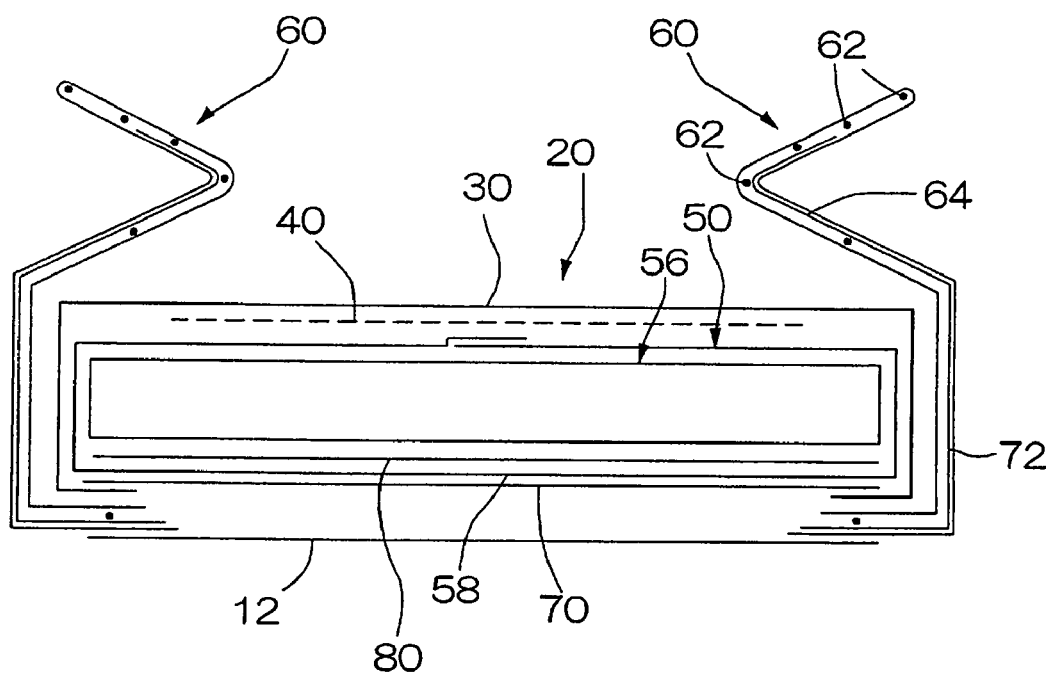
FIG. 3 is a plan view showing a pant-type diaper in a deployed state.
Figure 4:
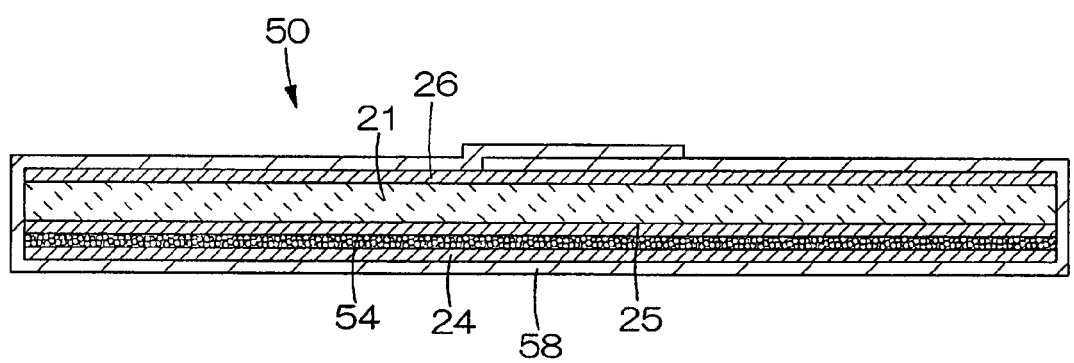
FIG. 4 is a sectional view showing a first preferred embodiment of an absorbent body.
Figure 5:
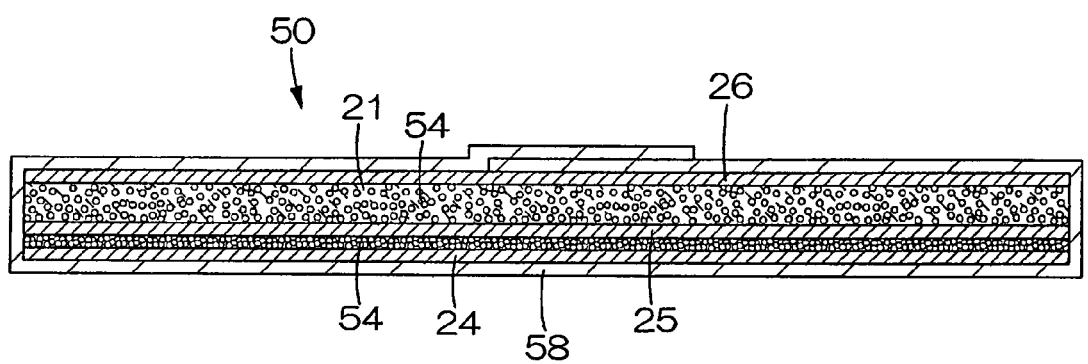
FIG. 5 is a sectional view showing a second preferred embodiment of an absorbent body.
Figure 6:
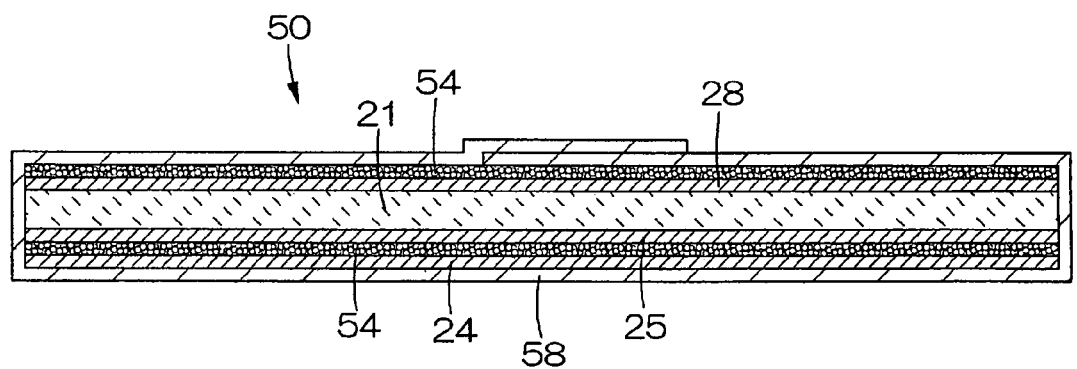
FIG. 6 is a sectional view showing a third preferred embodiment of an absorbent body.
Figure 7:
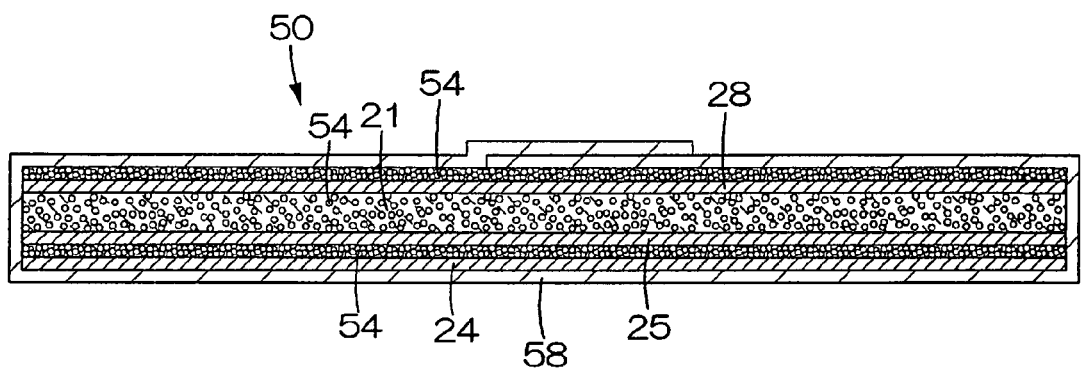
FIG. 7 is a sectional view showing a fourth preferred embodiment of an absorbent body.
Figure 8:
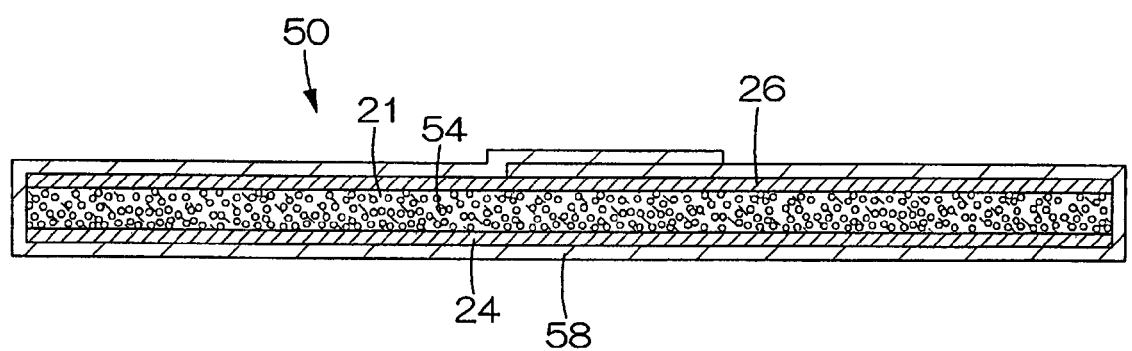
FIG. 8 is a sectional view showing a fifth preferred embodiment of an absorbent body.
Figure 9:
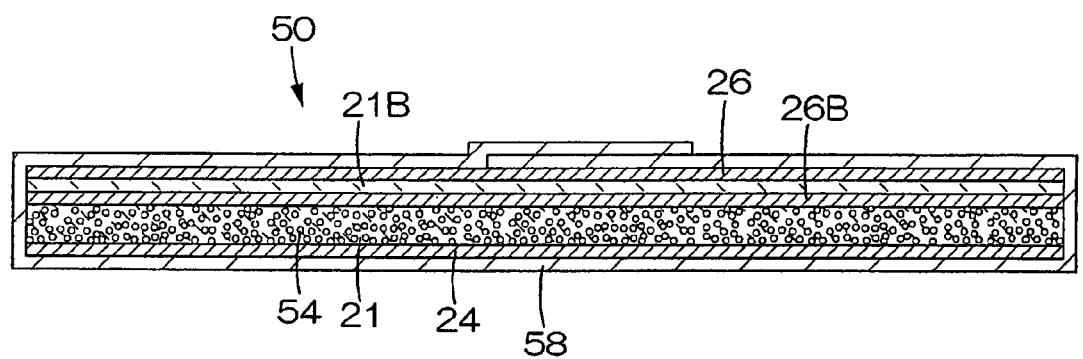
FIG. 9 is a sectional view showing a sixth preferred embodiment of an absorbent body.
Figure 10:
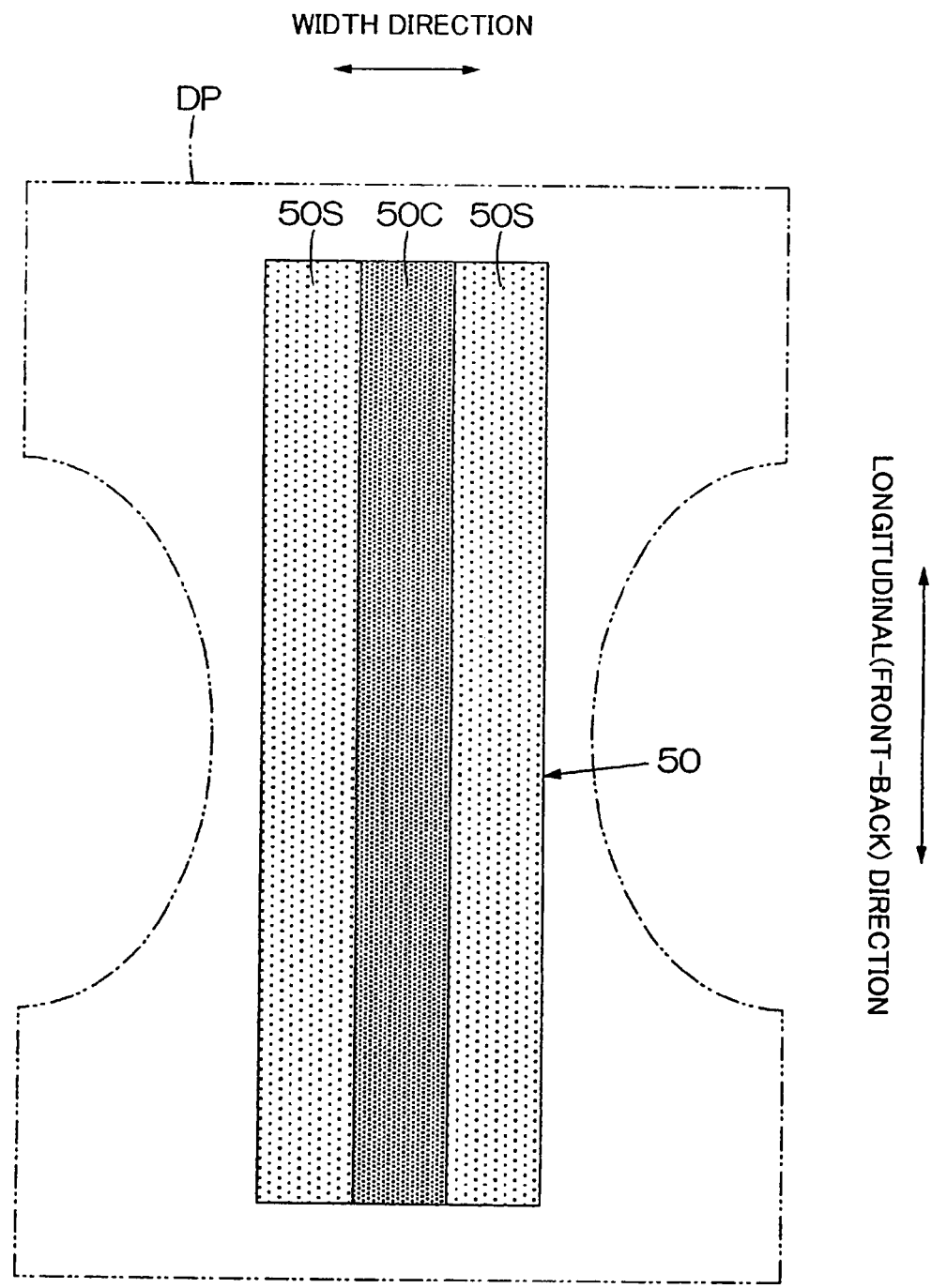
FIG. 10 is a plan view showing a seventh preferred embodiment of an absorbent body.
Figure 11:
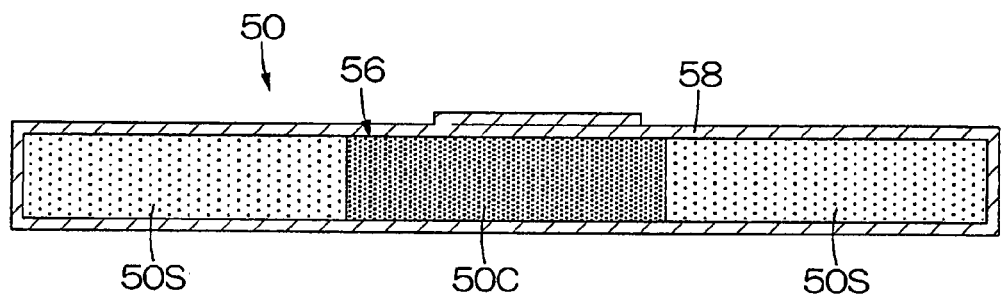
FIG. 11 is a sectional view showing the seventh embodiment of an absorbent body.
Figure 12:
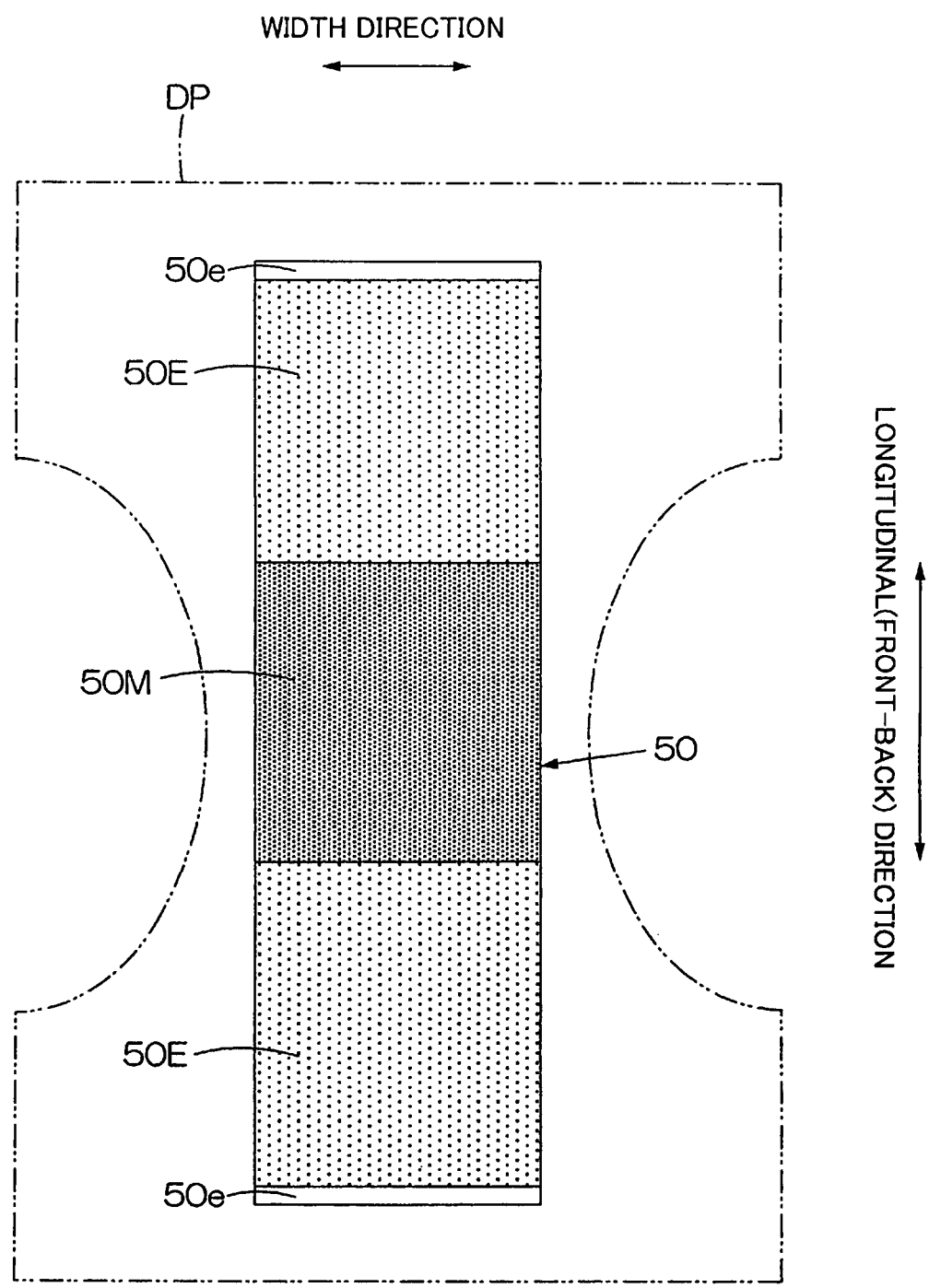
FIG. 12 is a plan view showing the seventh embodiment of an absorbent body.
Figure 13:
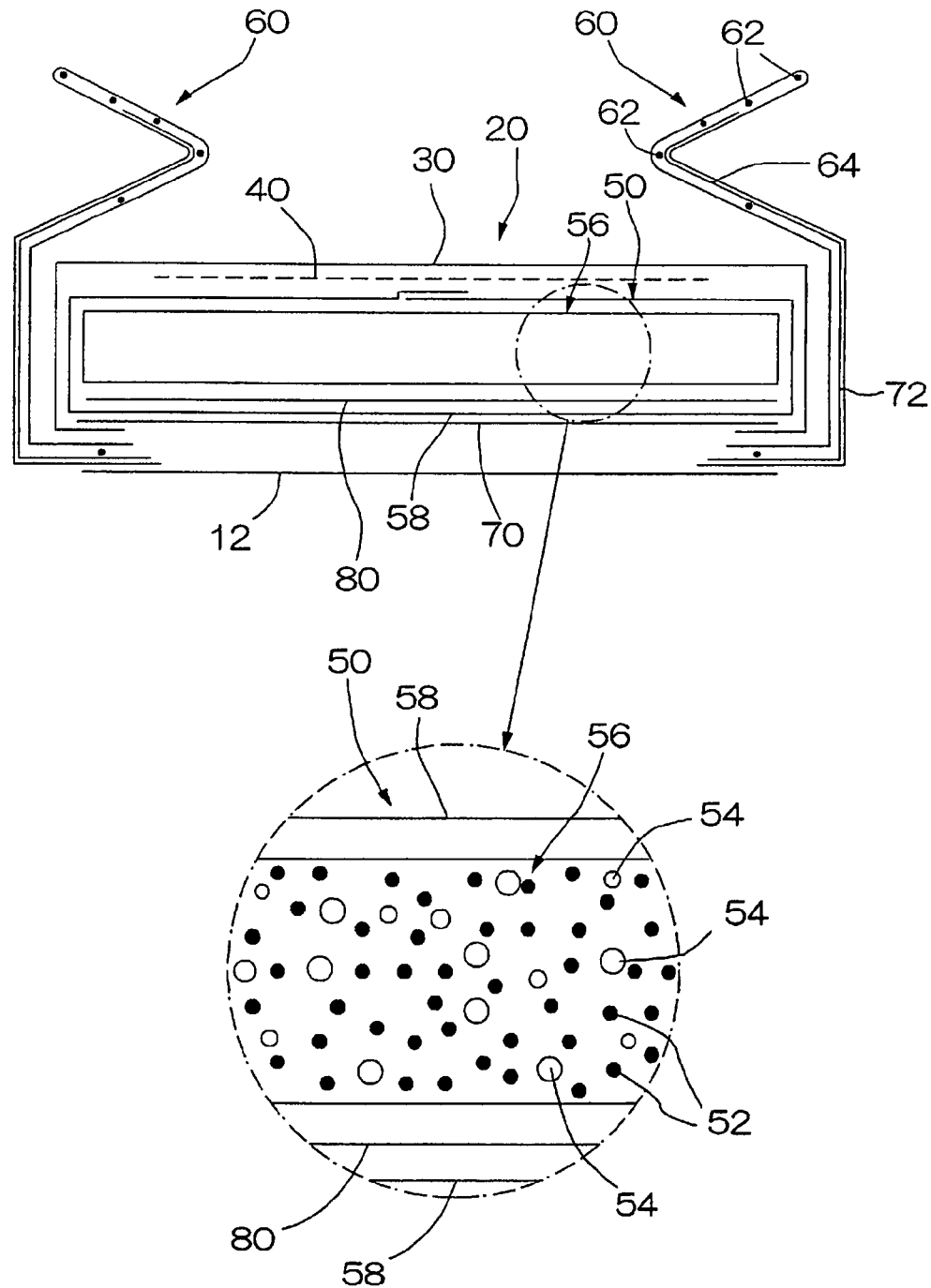
FIG. 13 is a sectional view showing the seventh embodiment of an absorbent body.
Figure 14:
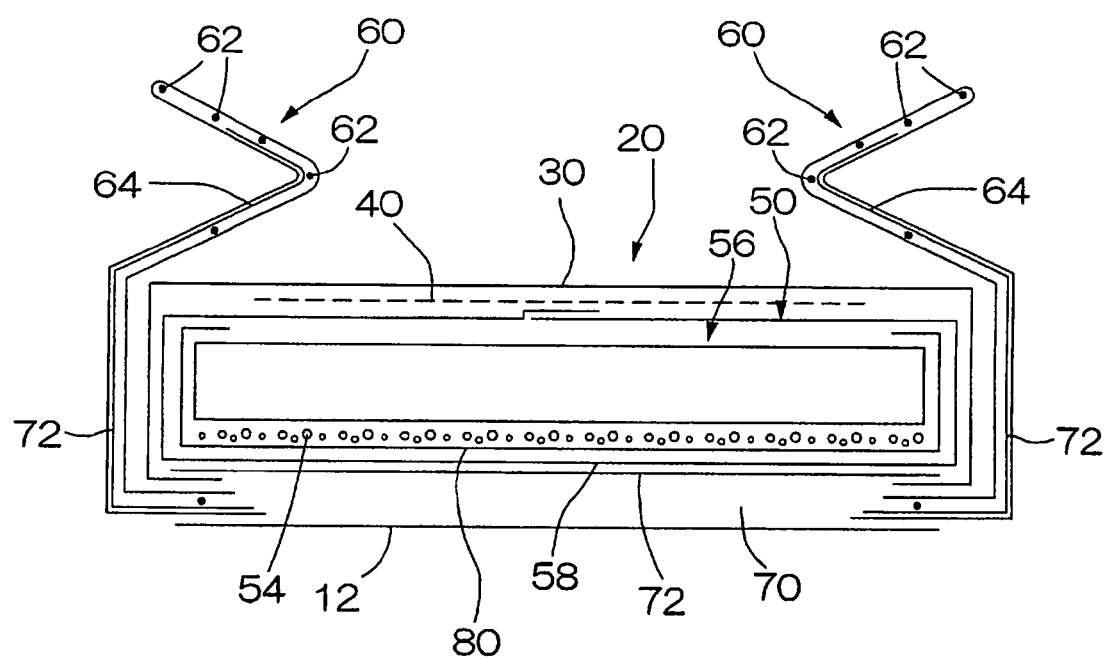
FIG. 14 is a sectional view showing the seventh embodiment of an absorbent body.
Figure 15:
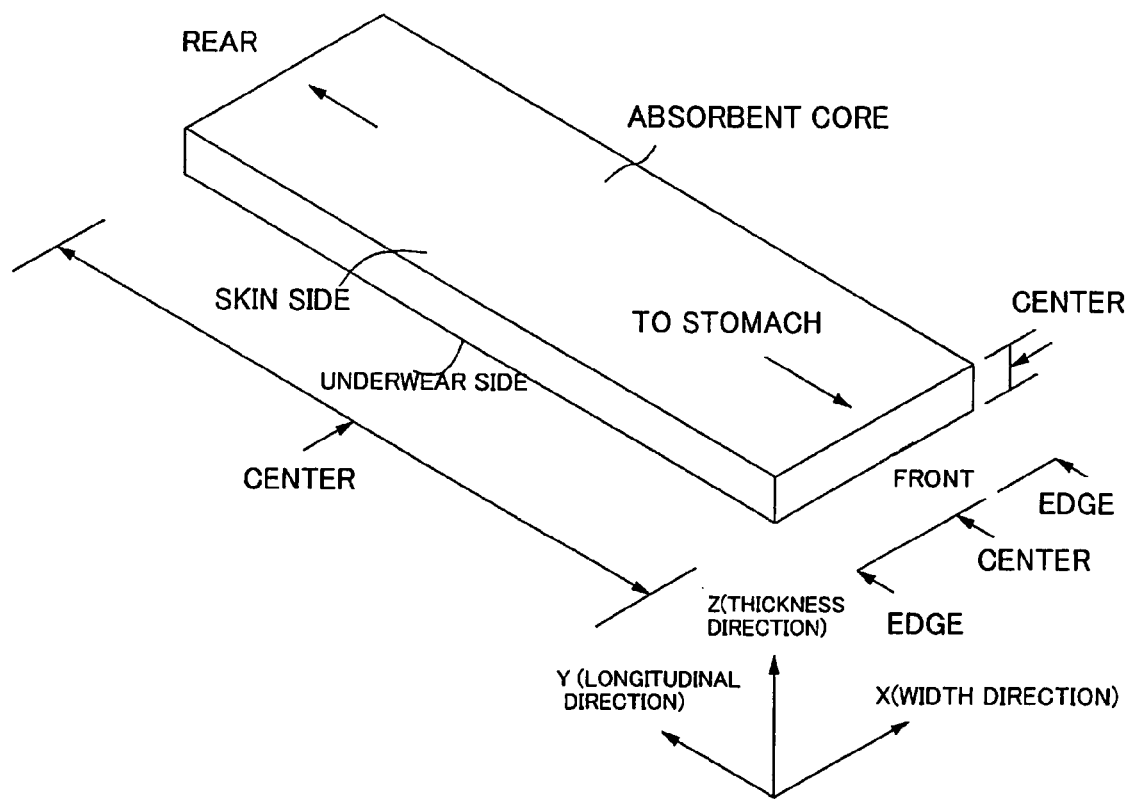
FIG. 15 is a schematic view for explaining directions of an absorbent body.
Figure 16:
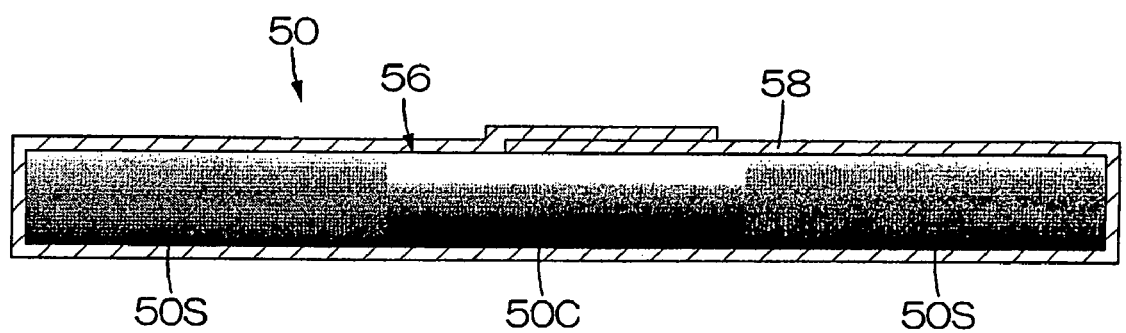
FIG. 16 is a sectional view showing an eighth preferred embodiment of an absorbent body.
Figure 17:
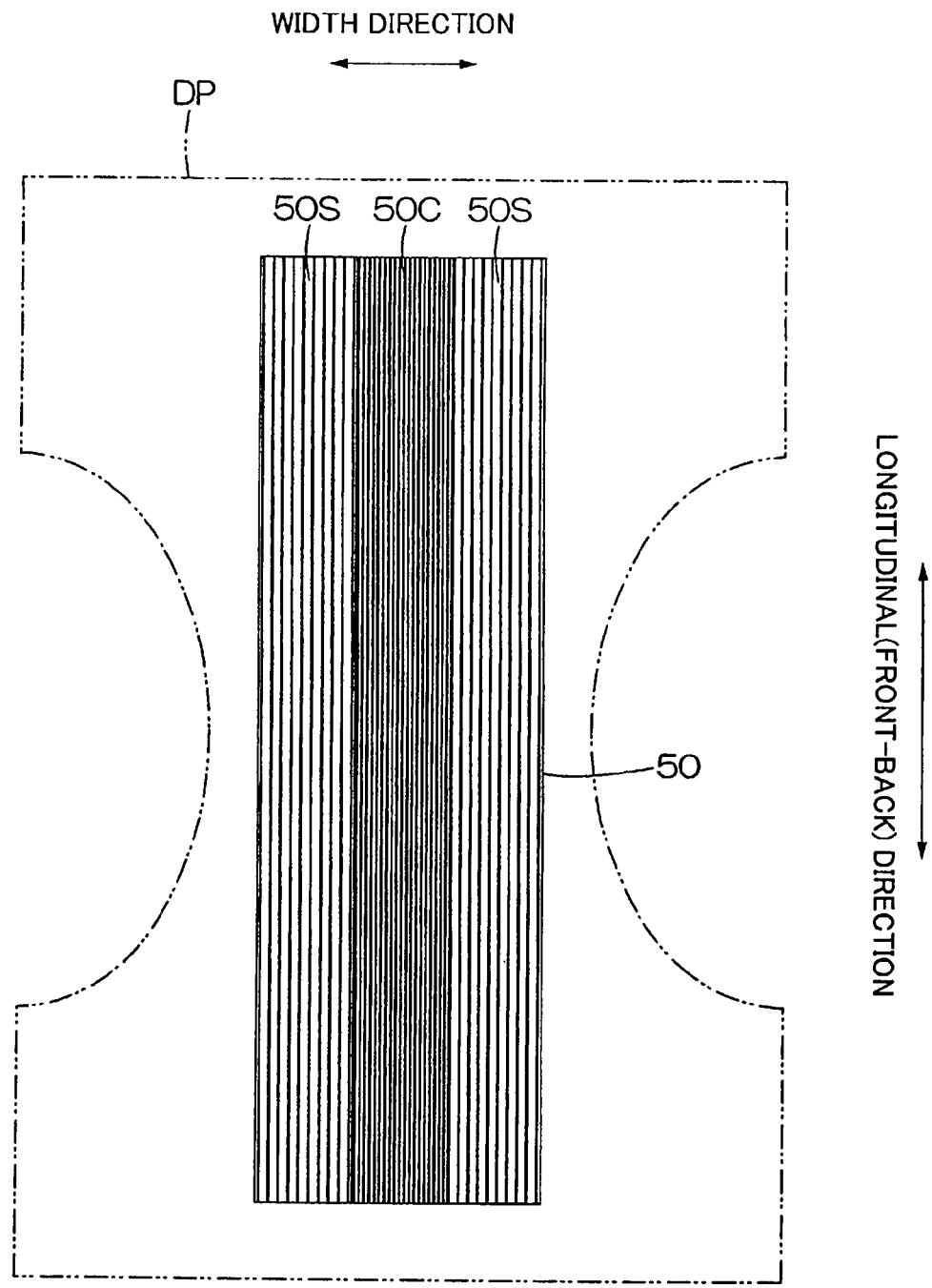
FIG. 17 is a sectional view showing a ninth preferred embodiment of an absorbent body.
Figure 18:
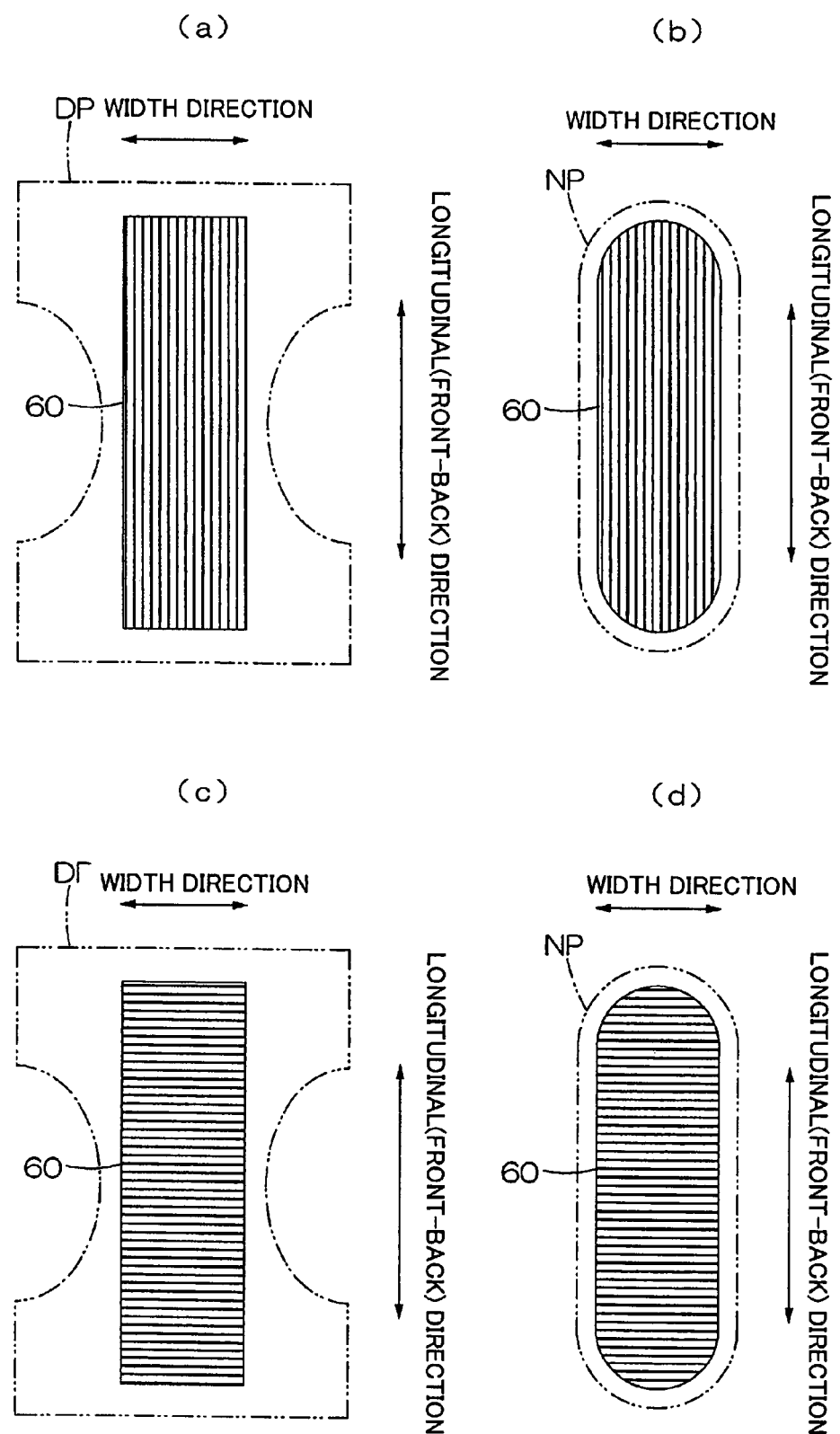
FIG. 18 is a plan view schematically showing the layout of an absorbent body.
Figure 19:
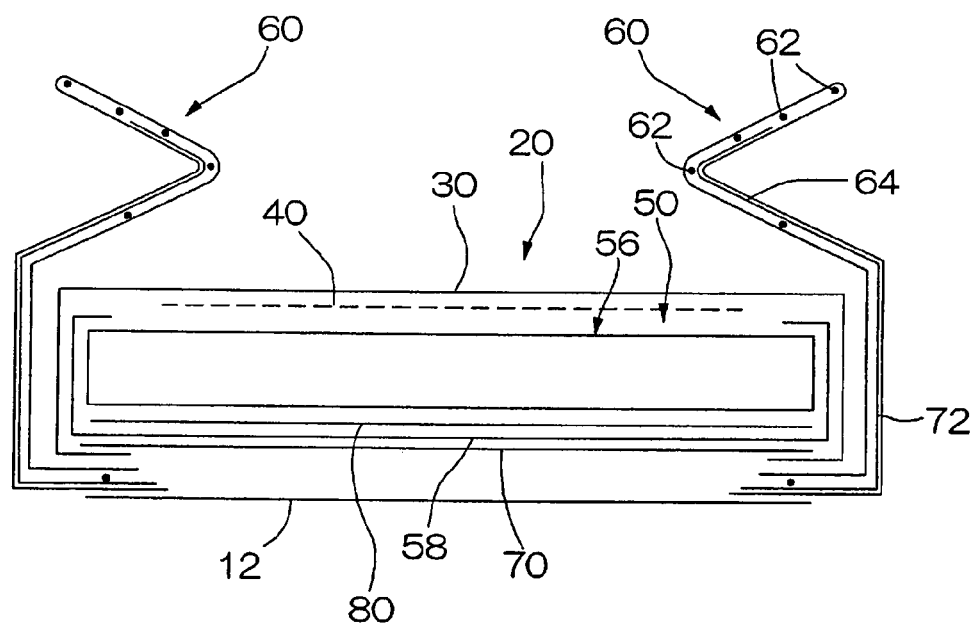
FIG. 19 is a sectional view showing another embodiment of an absorbent body.
Figure 20:
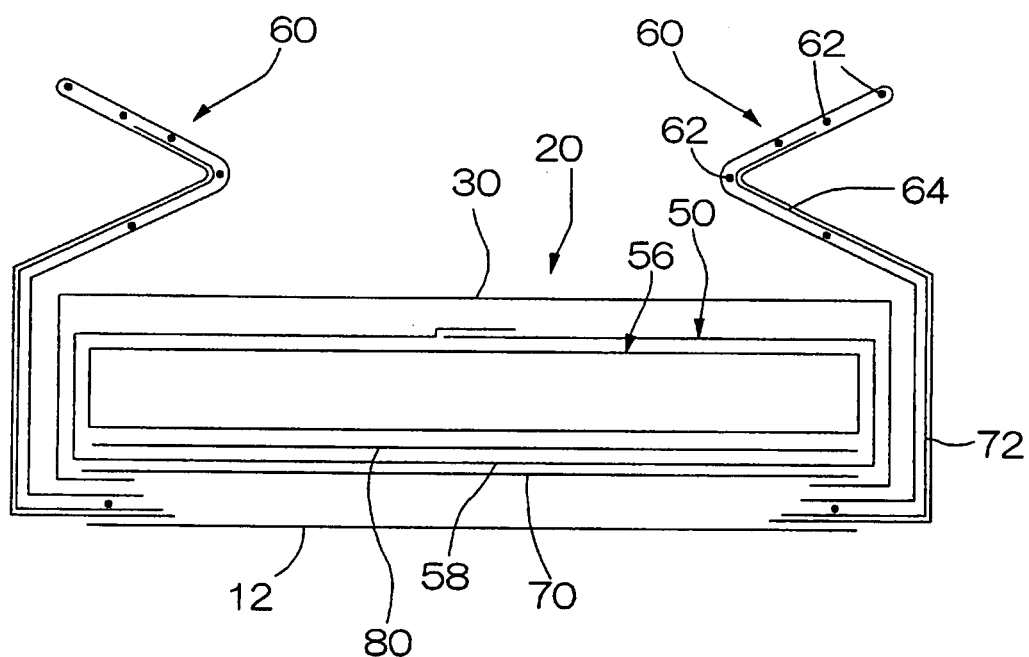
FIG. 20 is a sectional view showing another embodiment of an absorbent body.
Figure 21:
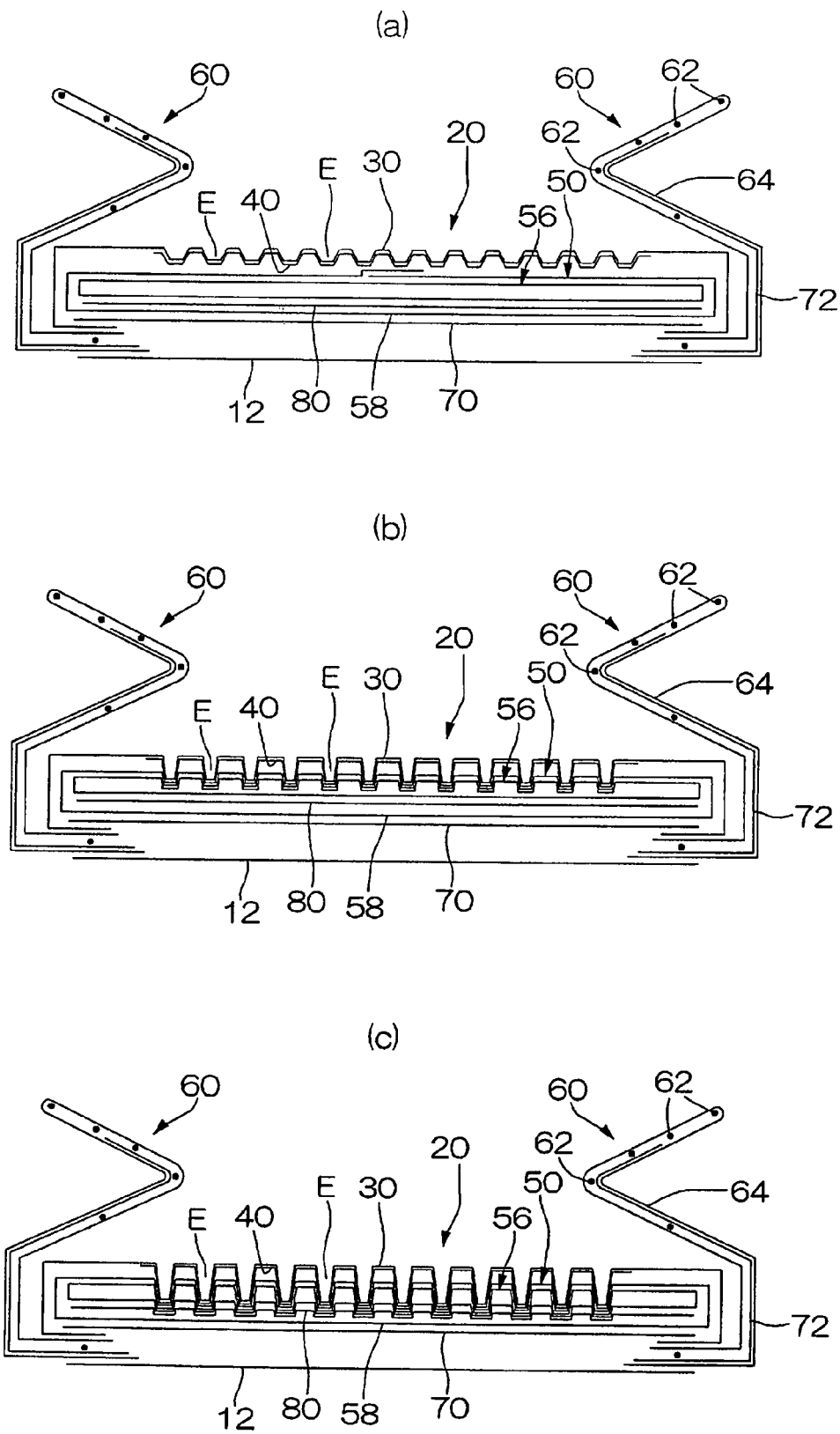
FIG. 21 is a sectional view showing another embodiment of an absorbent body.
Figure 22:
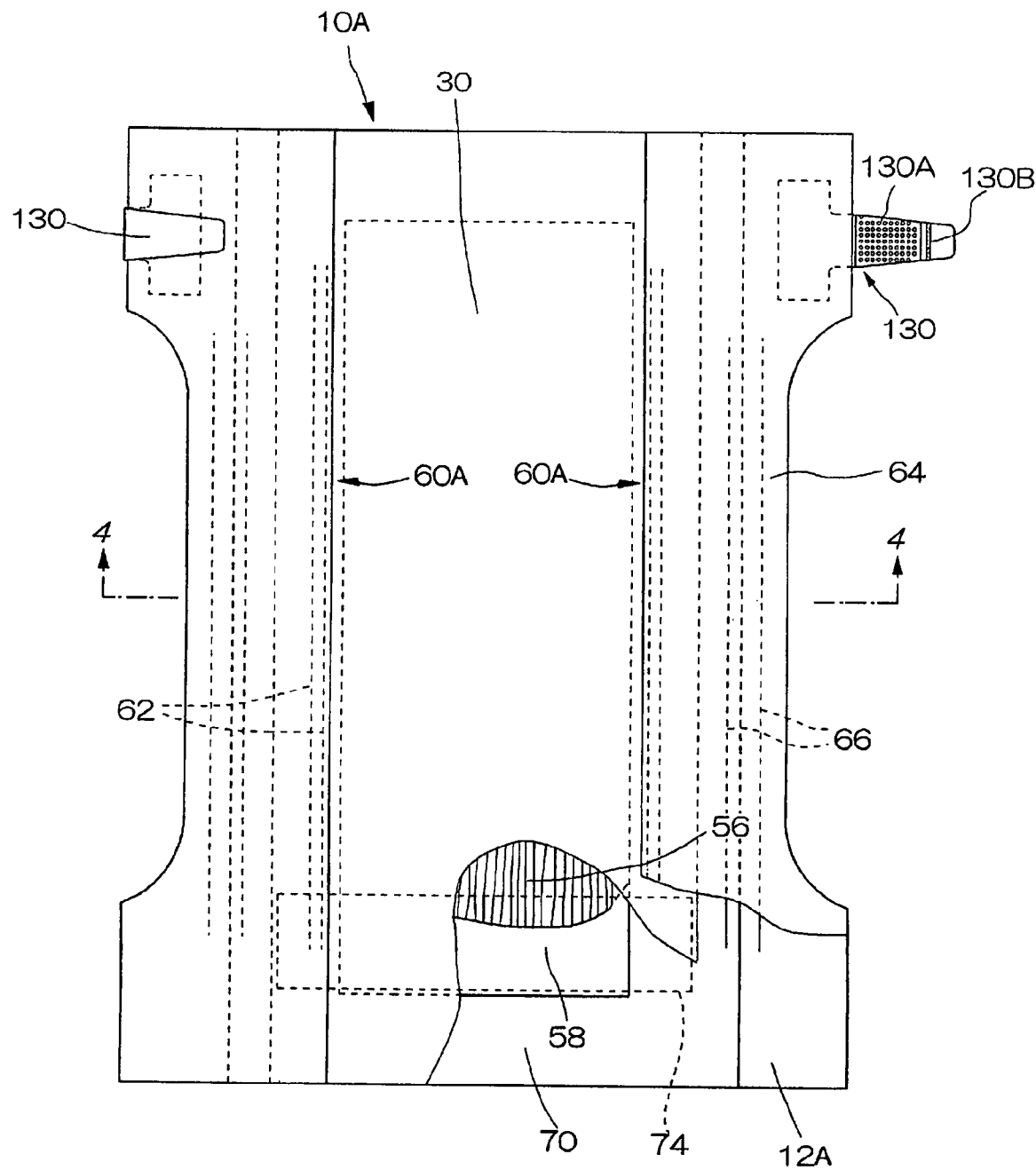
FIG. 22 is a plan view showing a tape-type diaper in a deployed state.
Figure 23:
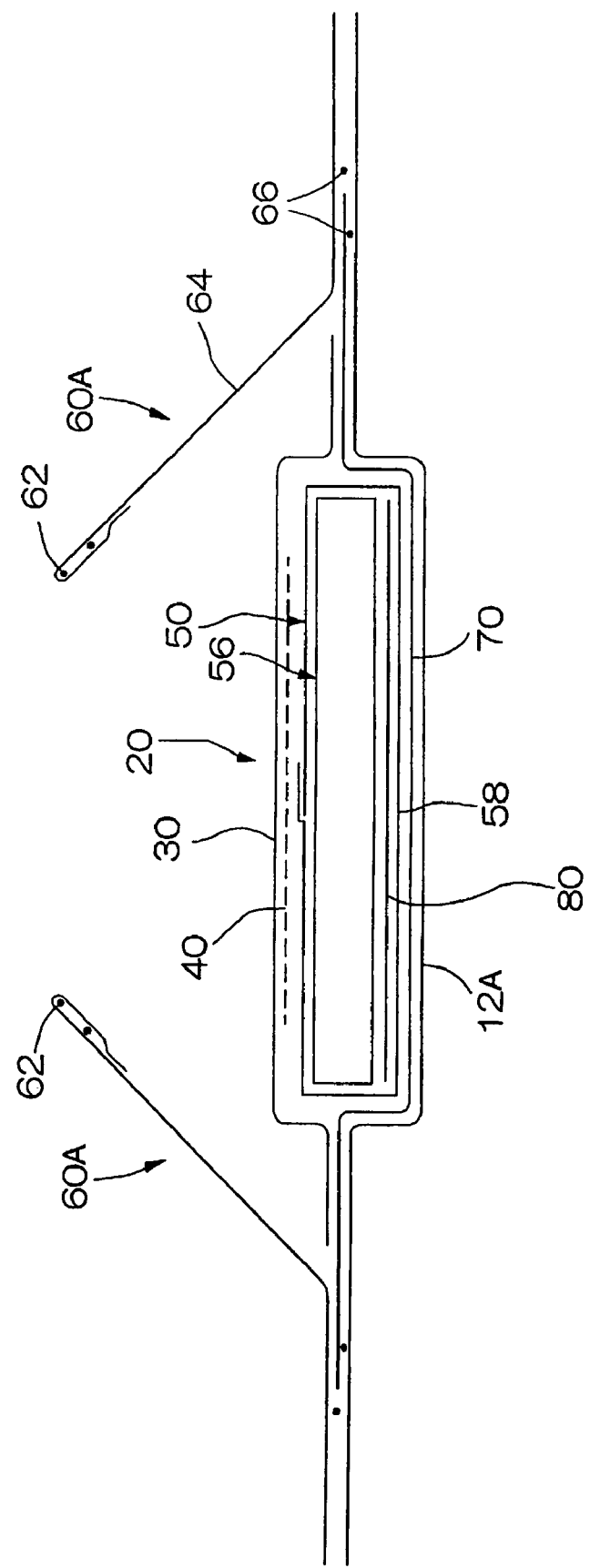
FIG. 23 is a sectional view taken along the line 4-4 of FIG. 22.
Figure 24:
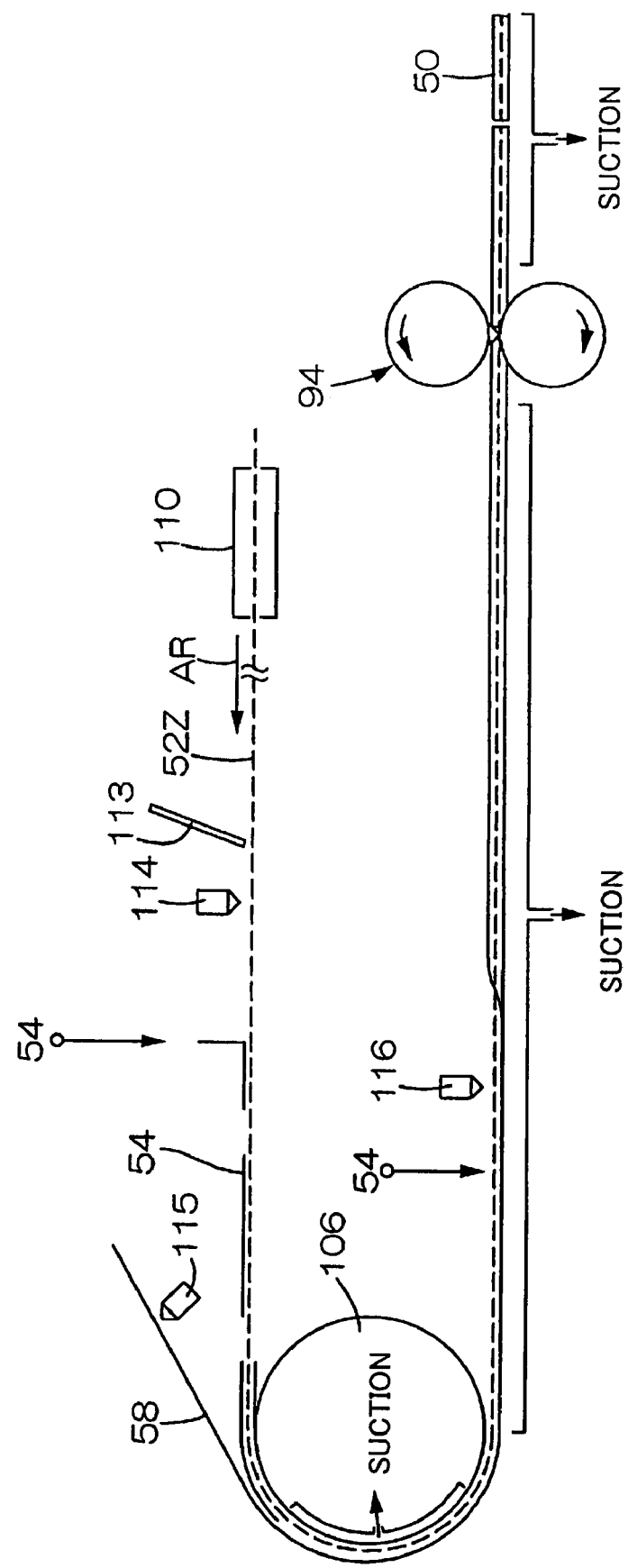
FIG. 24 is a schematic view showing a manufacturing facility example of an absorbent body.
Figure 25:
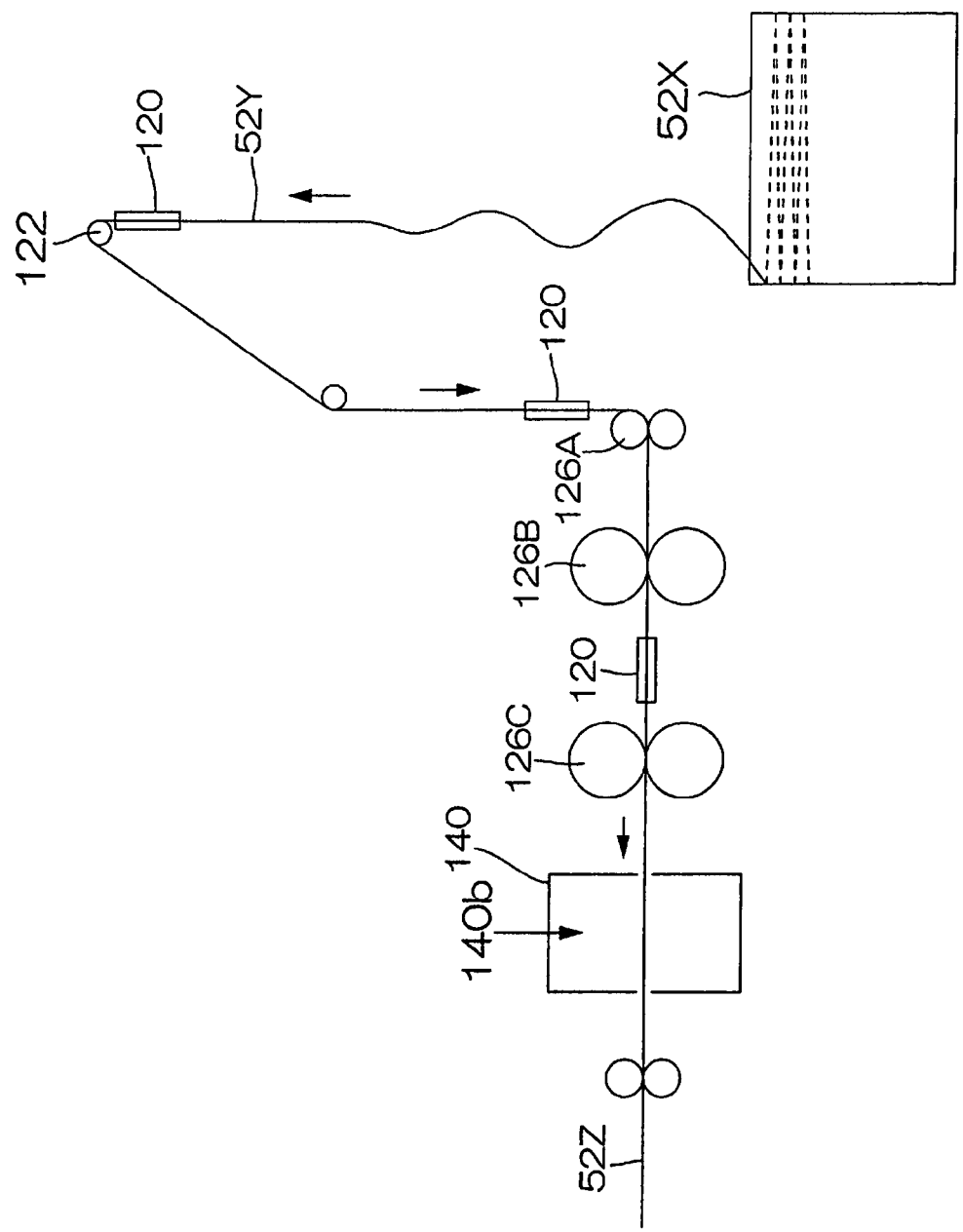
FIG. 25 is a schematic view showing an opening apparatus example.
Figure 26:
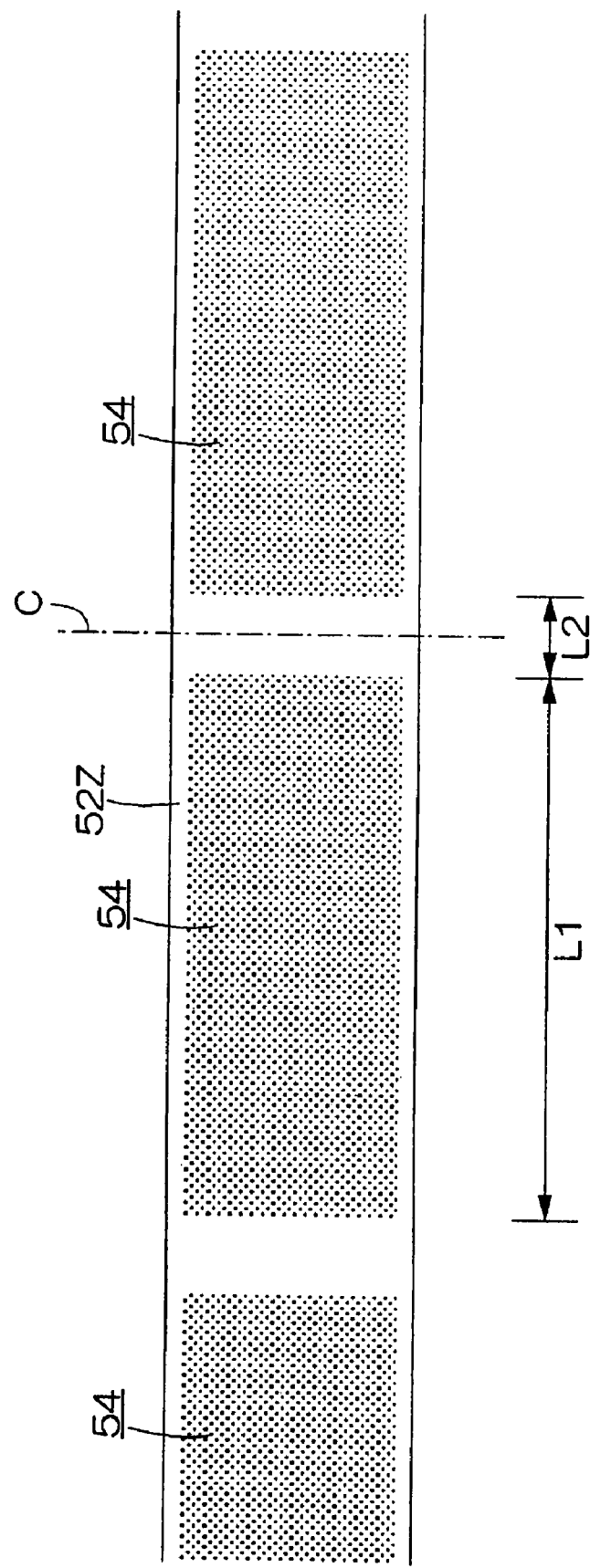
FIG. 26 is a schematic view showing the dispersion state of super absorbent polymer particles.
Figure 27:
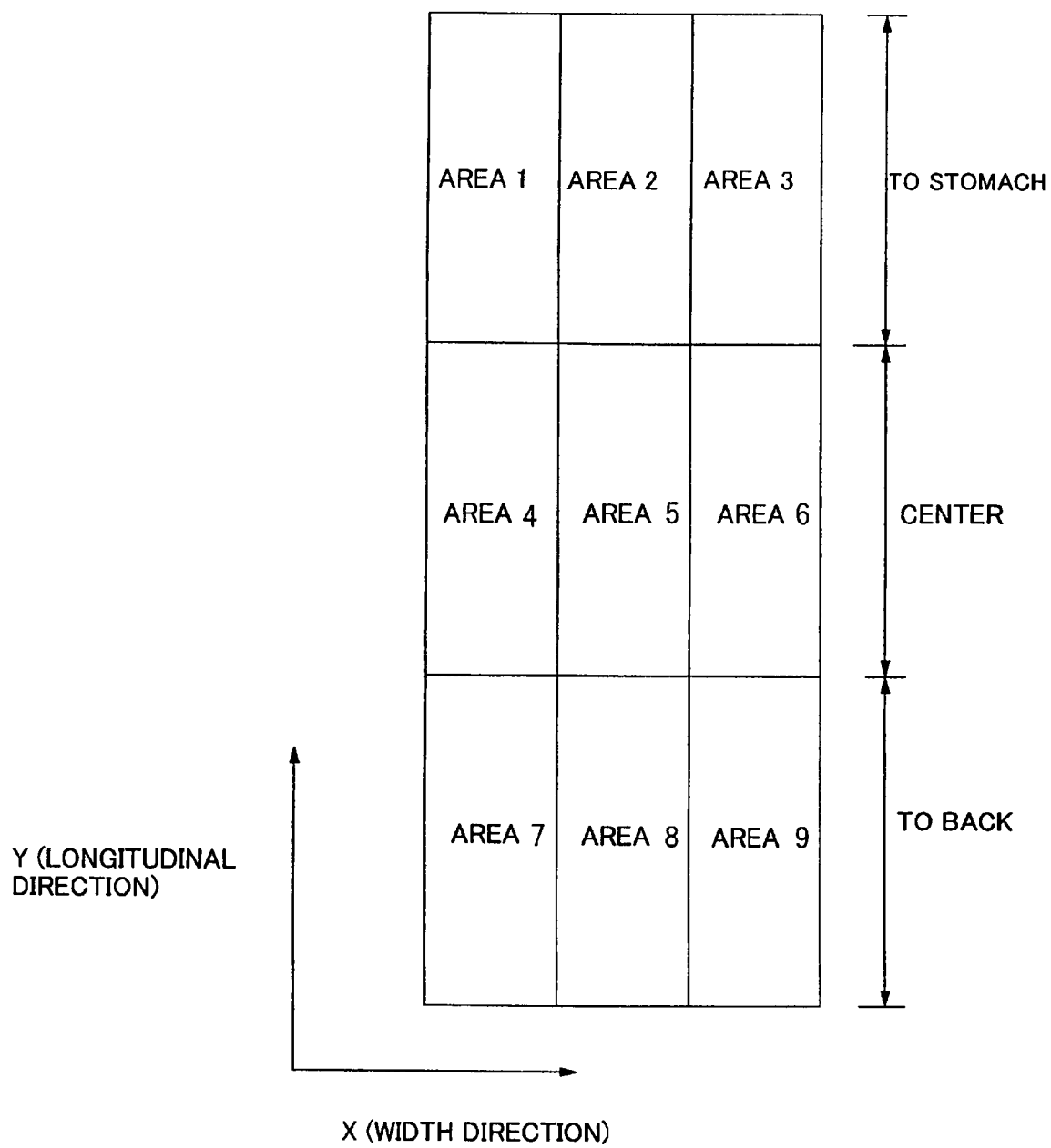
FIG. 27 is a schematic view for explaining directions of an absorbent body.
Figure 28:
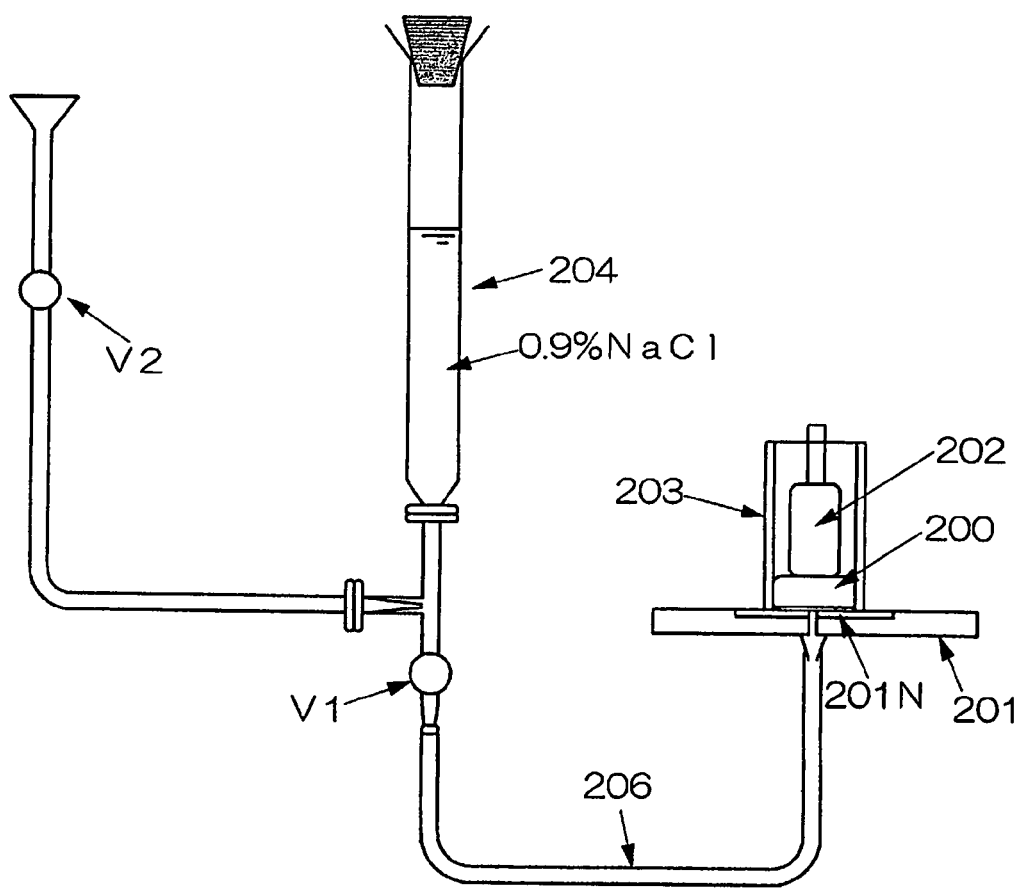
FIG. 28 is an explanatory view showing a tester.
Figure 29:
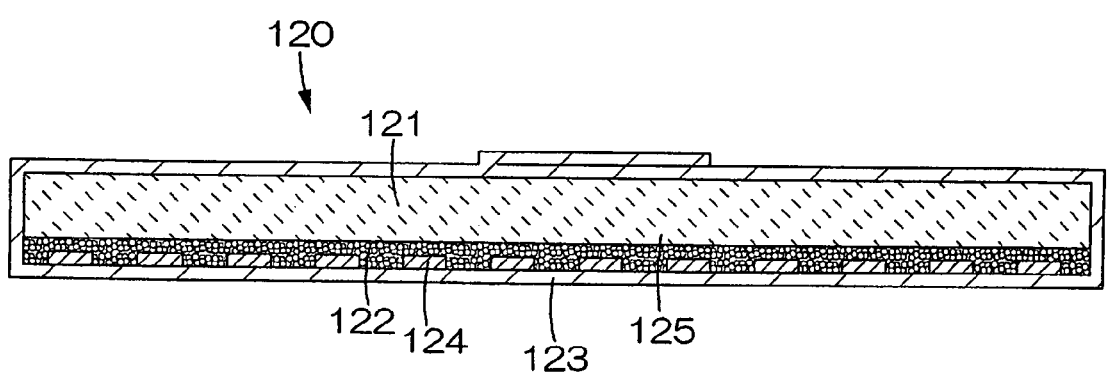
FIG. 29 is a sectional view showing a conventional example.

10: pant-type disposable diaper, 10A: tape-type disposable diaper, 12: exterior sheet, 12A: back sheet, 20: absorbent body, 30: top sheet, 40: intermediate sheet, 50: absorbent body, 52: filament, 52X: bale, 52Y: tow, 52Z: fiber aggregate, 54: super absorbent polymer particles, 56: absorbent core: 58: covering sheet, 60, 60A: barrier cuffs, 64: barrier sheet, 70: body fluid impermeable sheet, 72: second body fluid impermeable sheet, 80: holding sheet, 130: fastening piece, E: concave, and Z: super absorbent polymer particle dispersion zone.

The invention is claimed is:

1. An absorbent body manufacturing facility comprising;
a polymer application means for applying a super absorbent polymer particle to an outer surface of a fiber aggregate formed by opening a tow;
a polymer moving means for passing gas through a fiber aggregate applied with the super absorbent polymer particle to cause the super absorbent polymer particle to move into the fiber aggregate by a passing force of the gas; and
a means for providing an adhesive to the fiber aggregate before the super absorbent polymer particle is applied to the fiber aggregate, to the fiber aggregate after the super absorbent polymer particle is applied to the fiber aggregate as well as before the super absorbent polymer particle is moved into the fiber aggregate, or to the fiber aggregate after the super absorbent polymer particle is moved into the fiber aggregate,
wherein
there is provided a covering means for covering a surface applied with the super absorbent polymer article in the fiber aggregate with a sheet face;
the polymer moving means performs suction from a side opposite to a face covered with the sheet in the fiber aggregate; and
there is provided an absorbent body manufacturing facility comprising a means for shielding means for providing an adhesive to a face being on a side of the fiber aggregate in the sheet before covered with the sheet.

2. The absorbent body manufacturing facility according to claim 1, further comprising an opening means for opening a tow with compressed air to form a fiber aggregate, and a shielding means for shielding air flowing from the opening means to the means for providing an adhesive.

3. The absorbent body manufacturing facility according to claim 1, wherein
the polymer moving means exerts the passing force of the gas more strongly or in a longer time period with respect to a first portion of the fiber aggregate than a second portion of the fiber aggregate, the first portion being a width directional intermediate portion of the fiber aggregate, and the second portion being both width directional side portions of the fiber aggregate.

4. The absorbent body manufacturing facility according to claim 1, wherein
the polymer moving means exerts the passing force of the gas more strongly or in a longer time period with respect to a first portion of the fiber aggregate than a second portion of the fiber aggregate, the first portion being a longitudinal intermediate portion of the fiber aggregate, and the second portion being a front side portion and a rear side portion of the longitudinal intermediate portion of the fiber aggregate.

5. The absorbent body manufacturing facility according to claim 3, wherein
the polymer application means applies a super absorbent polymer particle so that an amount of the super absorbent polymer particle at the first portion of the fiber aggregate is larger than the amount of the super absorbent polymer at the second portion of the fiber aggregate.

6. The absorbent body manufacturing facility according to claim 1, further comprising a means for making a fiber density at a first portion of the fiber aggregate higher than a fiber density at a second portion of the fiber aggregate, the first portion being a width directional intermediate portion of the fiber aggregate, and the second portion being both width directional side portions of the fiber aggregate.

7. The absorbent body manufacturing facility according to claim 1, further comprising a means for making a fiber density at a first portion of the fiber aggregate higher than a fiber density at a second portion of the fiber aggregate, the first portion being a longitudinal intermediate portion of the fiber aggregate, and the second portion being a front side portion and a rear side portion of the longitudinal intermediate portion of the fiber aggregate.

8. The absorbent body manufacturing facility according to claim 1, further comprising a conveyer line for conveying a fiber aggregate formed by opening a tow, and the polymer application means applying the super absorbent polymer particle while periodically changing an application amount with respect to a fiber aggregate on the conveyor line.

9. The absorbent body manufacturing facility according to claim 8, wherein the polymer application means intermittently applies the super absorbent polymer particle in a conveying direction to provide alternately in a conveying direction a portion where the super absorbent polymer particle is applied and a portion where the super absorbent polymer particle is not applied; and there is provided a cutter for cutting the fiber aggregate into individual absorbent bodies at the portion where the super absorbent polymer particle is not applied.

10. The absorbent body manufacturing facility according to claim 4, wherein the polymer application means applies a super absorbent polymer particle so that an amount of the super absorbent polymer particle at the first portion of the fiber aggregate is larger than an amount of the super absorbent polymer at the second portion of the fiber aggregate.

\* \* \* \* \*